(12) United States Patent
Kuo

(10) Patent No.: US 6,623,698 B2
(45) Date of Patent: Sep. 23, 2003

(54) SALIVA-MONITORING BIOSENSOR ELECTRICAL TOOTHBRUSH

(76) Inventor: Youti Kuo, 88 Foxbourne Rd., Penfield, NY (US) 14526

( * ) Notice: Subject to any disclaimer, the term of this patent is extended or adjusted under 35 U.S.C. 154(b) by 346 days.

(21) Appl. No.: 09/802,988

(22) Filed: Mar. 12, 2001

(65) Prior Publication Data

US 2002/0127143 A1 Sep. 12, 2002

(51) Int. Cl.7 .................................................. G01N 15/06
(52) U.S. Cl. ...................... 422/68.1; 422/55; 422/58; 422/82.01; 422/82.02; 422/82.05; 600/573; 600/582; 600/584; 600/309
(58) Field of Search ........................ 422/68.1, 55, 58, 422/82.02, 82.05, 82.09, 69, 82.01; 600/584, 573, 578, 582, 309

(56) References Cited

U.S. PATENT DOCUMENTS

| | | |
|---|---|---|
| 3,968,011 A | 7/1976 | Manautou et al. |
| 4,105,522 A | 8/1978 | Friedenberg et al. |
| 4,385,125 A | 5/1983 | Preti et al. |
| 4,786,596 A | 11/1988 | Adams |
| 4,834,110 A | 5/1989 | Richard |
| 5,100,620 A | 3/1992 | Brenneman |
| 5,120,420 A | 6/1992 | Nankai et al. |
| 5,206,711 A | 4/1993 | Berthold et al. |
| 5,208,147 A | 5/1993 | Kagenow et al. |
| 5,264,103 A | 11/1993 | Yoshioka et al. |
| 5,335,305 A | 8/1994 | Kosa et al. |
| 5,480,776 A | 1/1996 | Dullien |
| 5,500,374 A | 3/1996 | Wenzhi |
| 5,573,798 A | 11/1996 | Kato et al. |
| 5,684,296 A | 11/1997 | Hamblin et al. |
| 5,695,930 A | 12/1997 | Weinstein et al. |
| 5,851,838 A | 12/1998 | Vetter et al. |
| 5,909,977 A | 6/1999 | Kuo |
| 5,968,746 A | 10/1999 | Schneider |
| 5,988,426 A | 11/1999 | Stern |
| 5,997,817 A | 12/1999 | Crismore et al. |
| 6,004,441 A | 12/1999 | Fujiwara et al. |
| 6,058,934 A | 5/2000 | Sullivan |
| 6,061,586 A | 5/2000 | Kuperman et al. |
| 6,080,118 A | 6/2000 | Blythe |
| 6,099,484 A | 8/2000 | Douglas et al. |
| 6,102,872 A | 8/2000 | Doneen et al. |
| 6,176,903 B1 | 1/2001 | Wamsiedler |

FOREIGN PATENT DOCUMENTS

JP          2002-181812       *   6/2002

* cited by examiner

*Primary Examiner*—Jill Warden
*Assistant Examiner*—Sam P. Siefke
(74) *Attorney, Agent, or Firm*—Fred L. Denson

(57) ABSTRACT

A biosensor electrical toothbrush having a brush head with a test channel and a renewable biosensor system within the test channel for performing routine saliva tests. The brush head stimulates saliva production and collection in the test channel where measurement signals are produced by sensors. The signals are transmitted for storage and analysis to a microprocessor that provides readable data signals reflective of the presence or quantitative level of a specific component of saliva. The brush handle contains the microprocessor, a display means, a battery, a motor and a reservoir for storing a reagent which is supplied in controlled quantities to the channel during saliva testing. The toothbrush is used to detect fertility periods, pregnancy, labor onset, alcohol concentration, blood glucose concentration and indicators that signal a need for comprehensive HIV testing. A test head without bristles may be used in place of a brush head to provide a saliva-monitoring oral device which performs the same saliva tests as the electrical toothbrush. The bristles are replaced by an oral thermometer, a gum massage element or other element used for medical or dental functions.

24 Claims, 20 Drawing Sheets

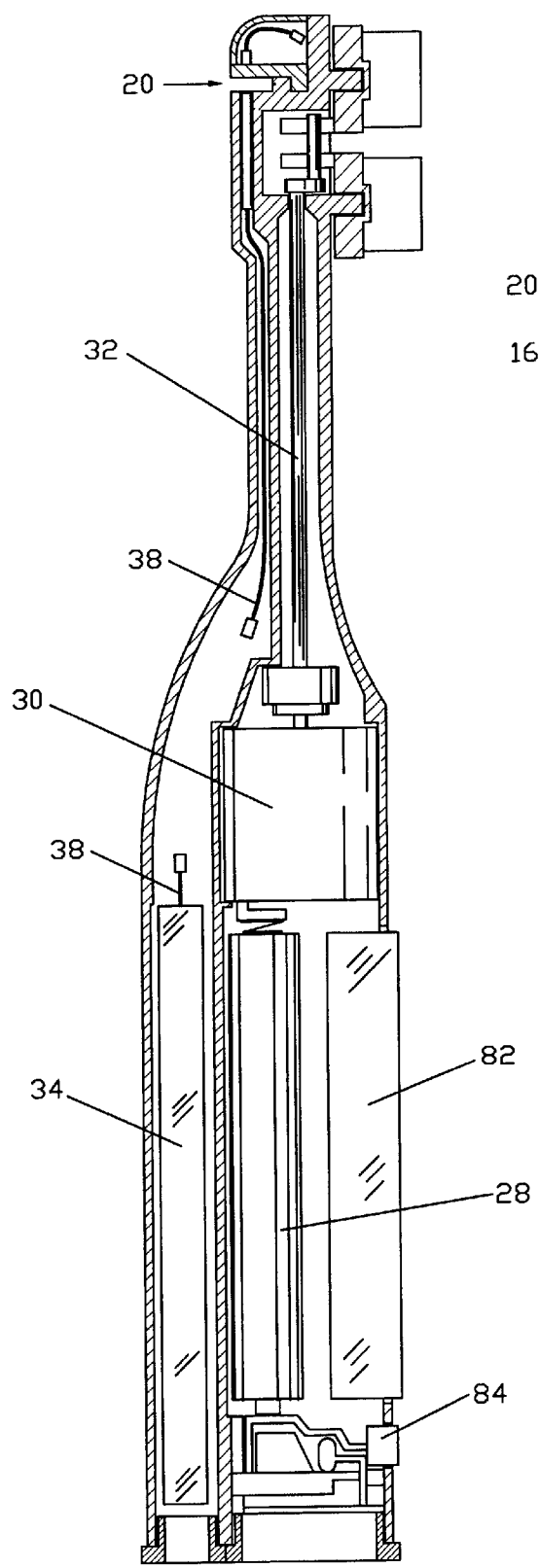
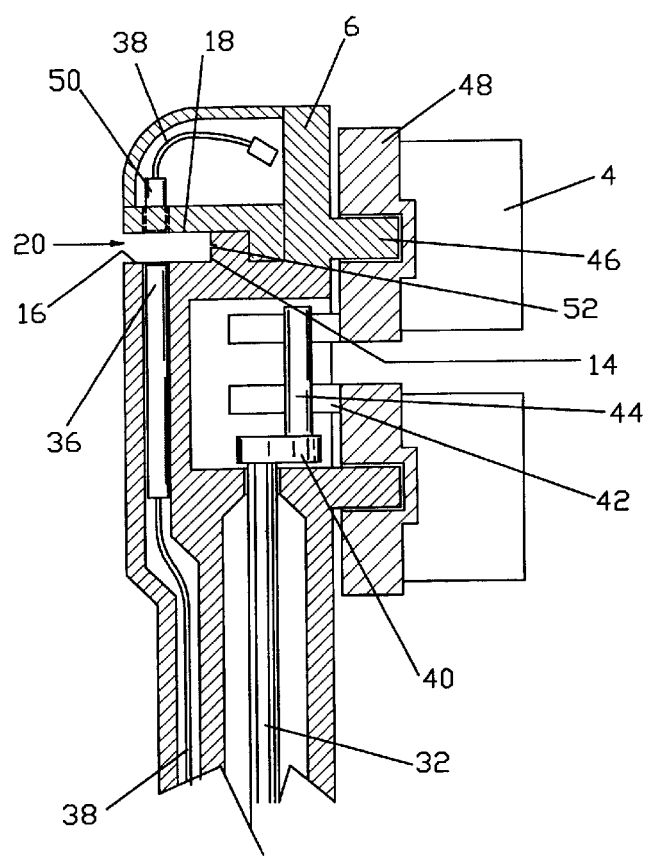
Fig. 1b
Fig. 1a

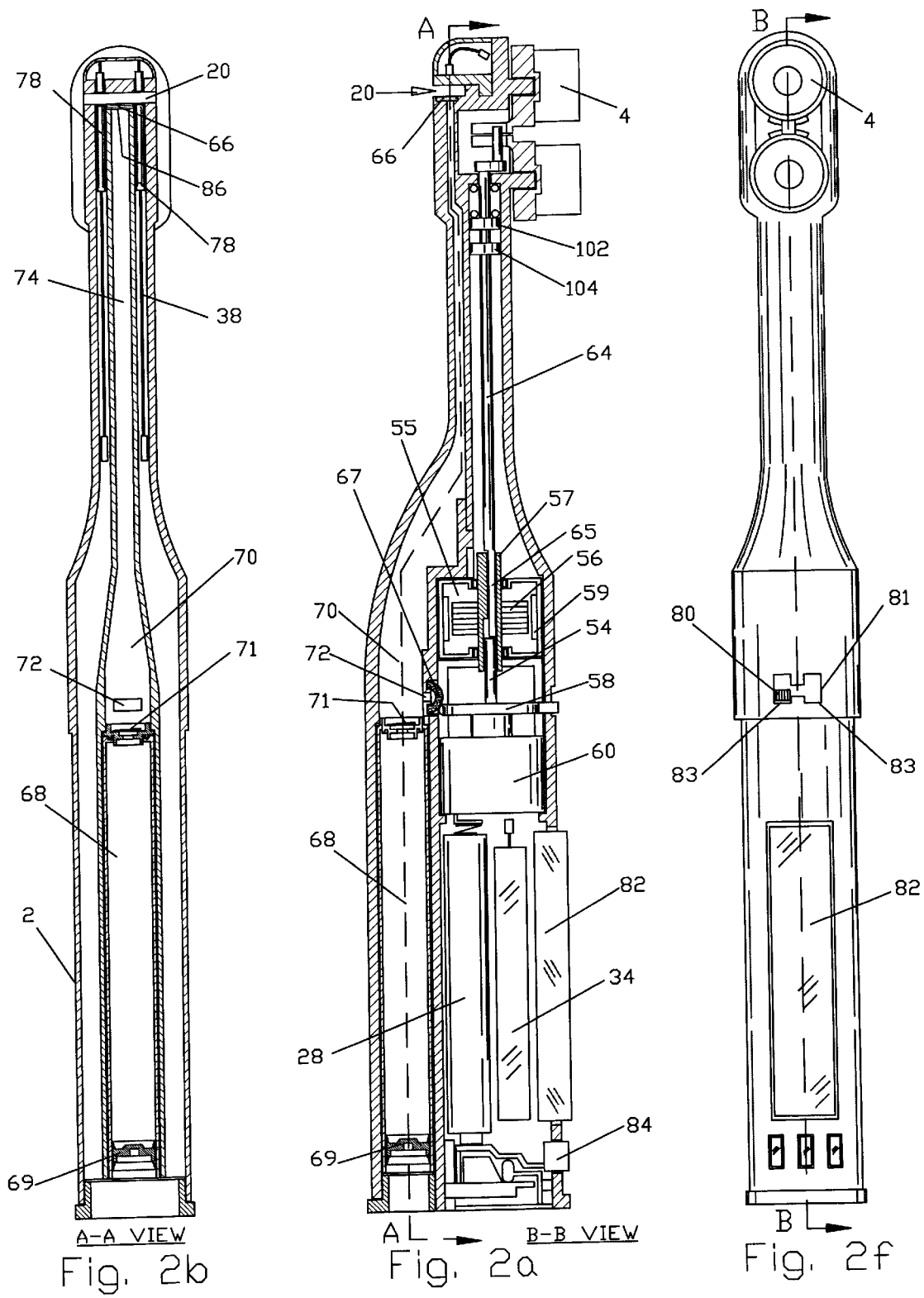

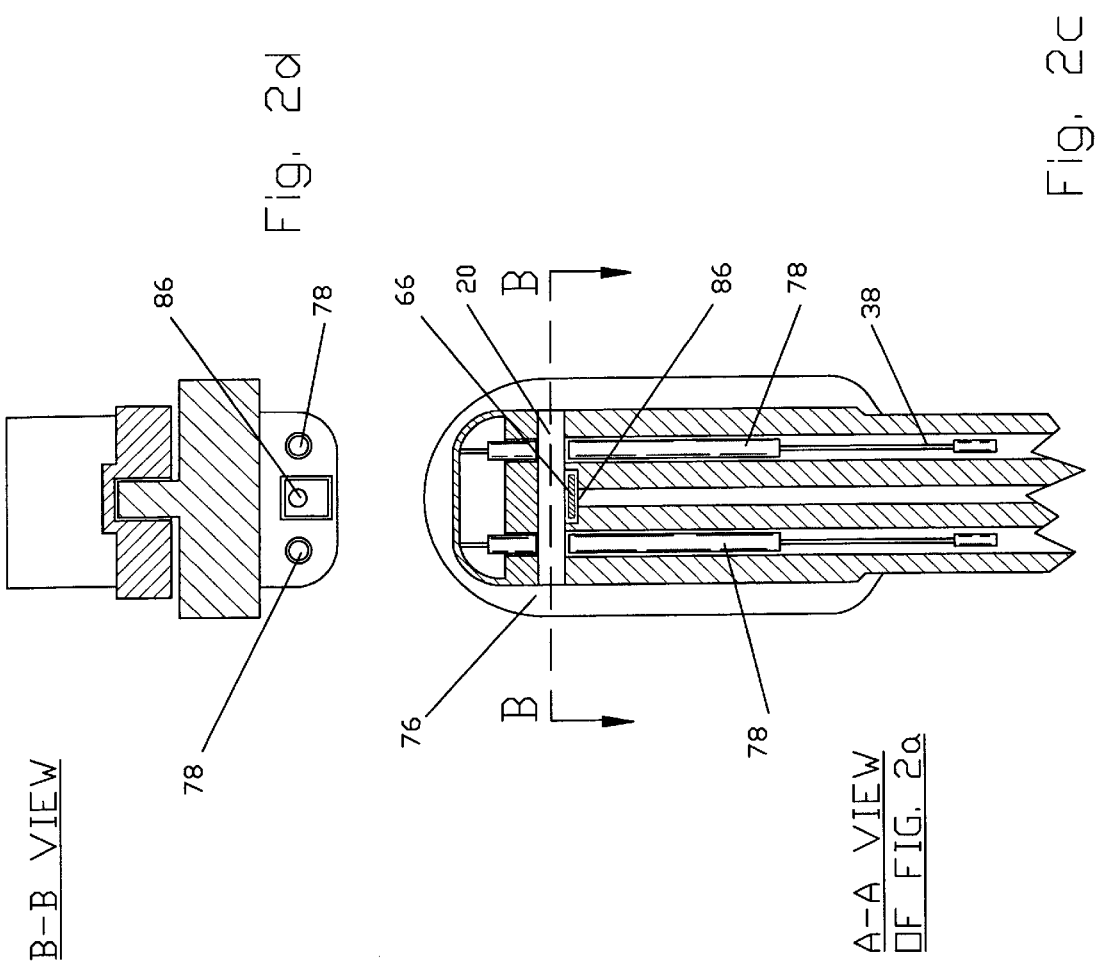

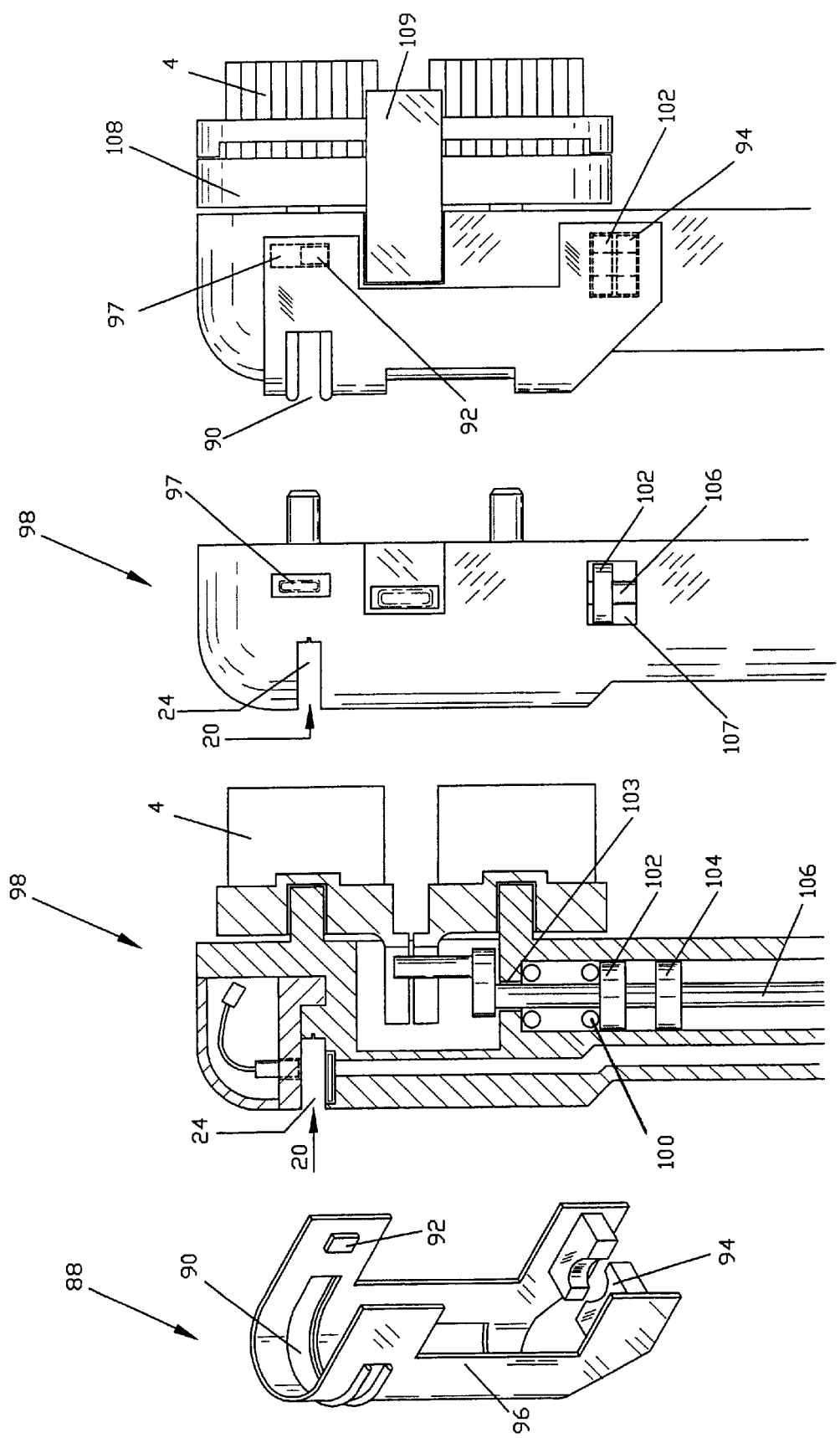

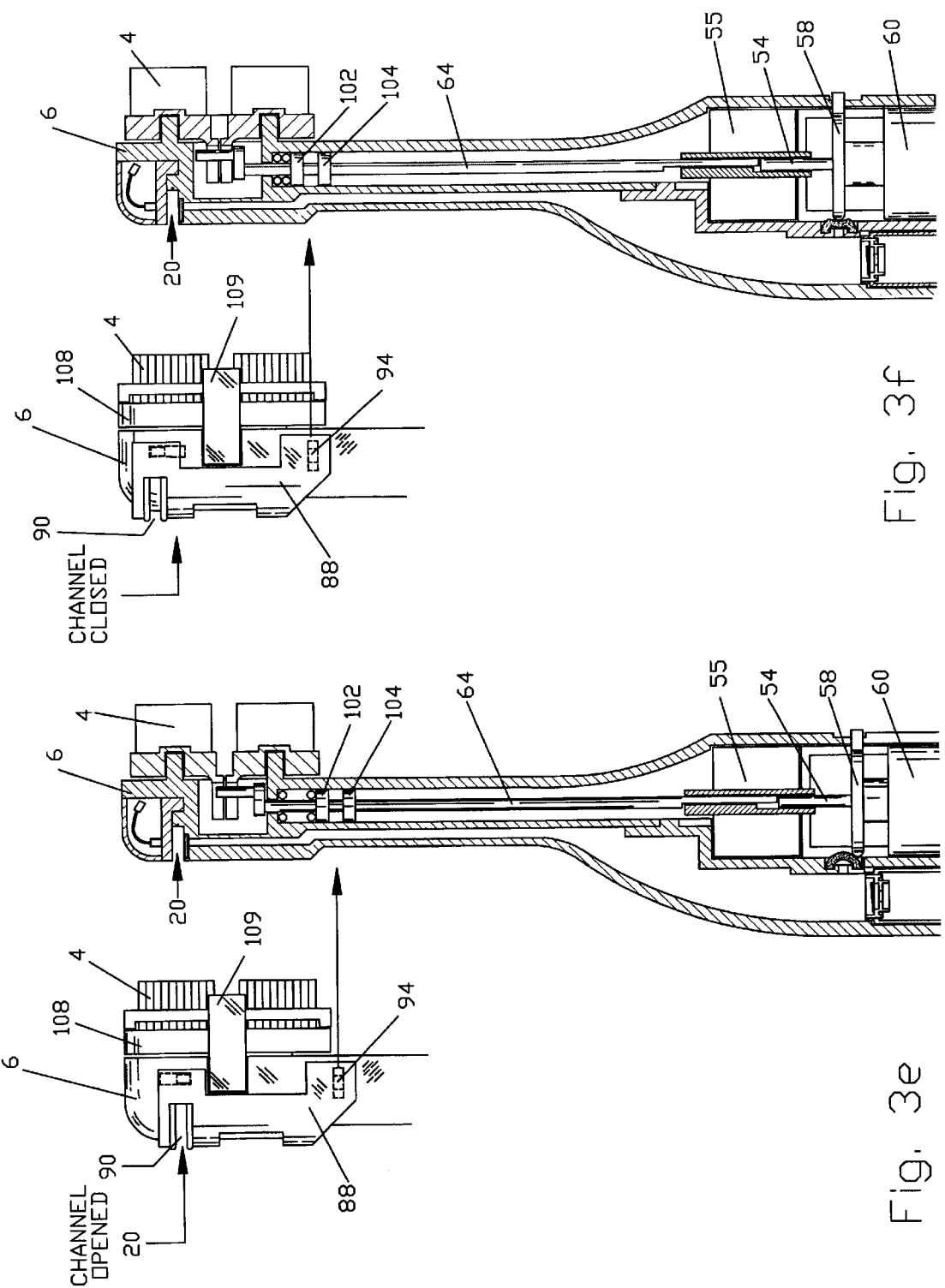

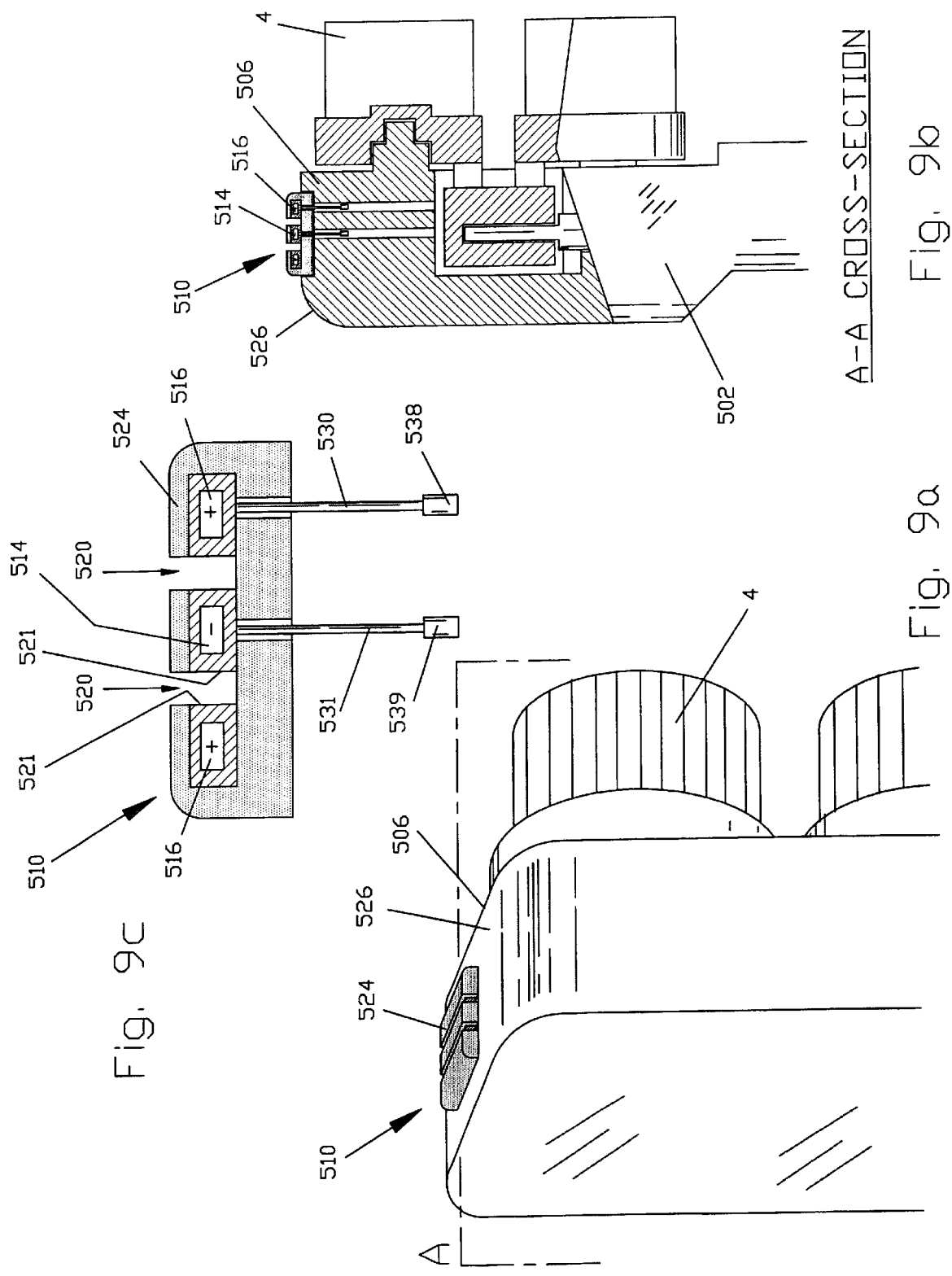

A-A CROSS-SECTION

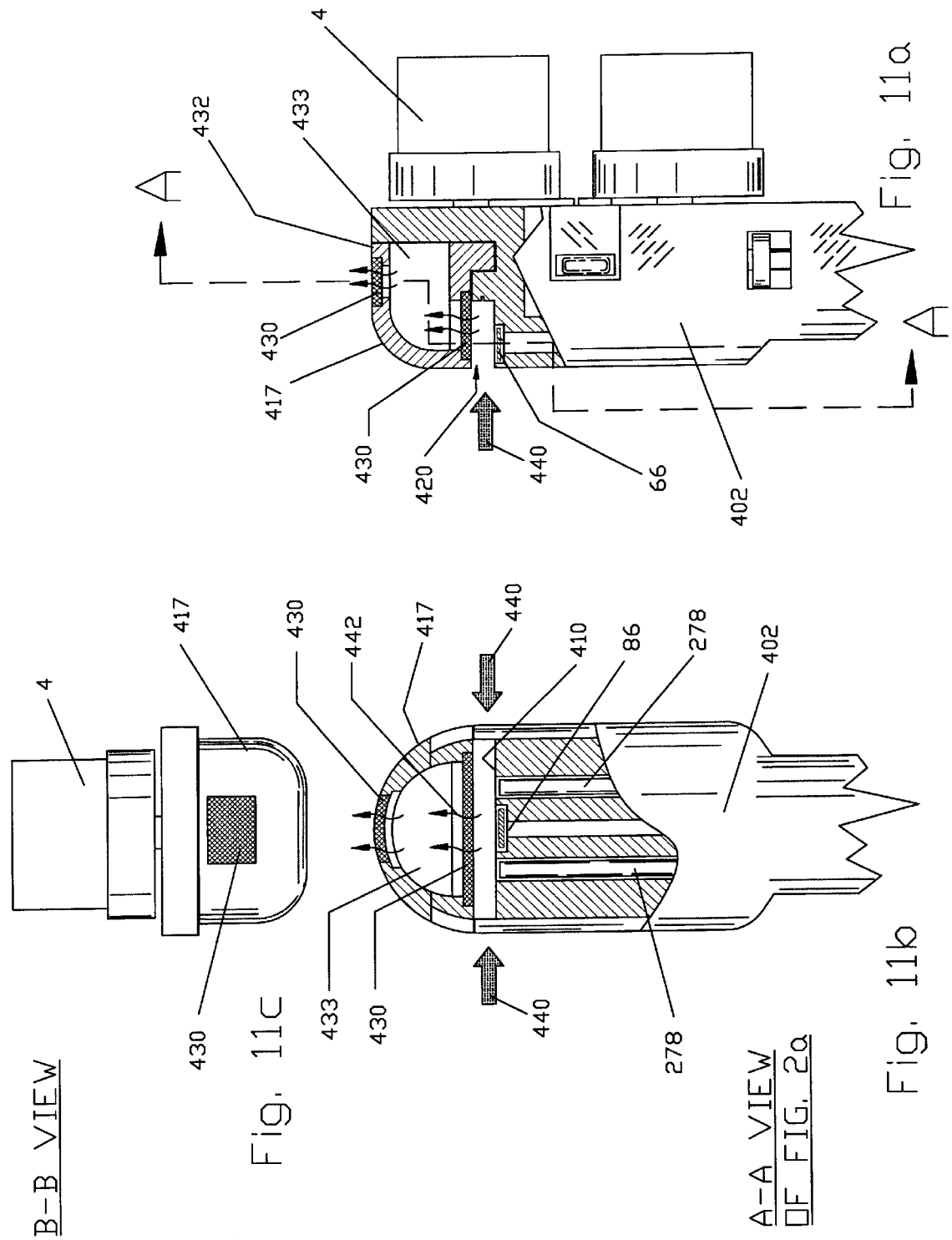

SALIVA-MONITORING BIOSENSOR ELECTRICAL TOOTHBRUSH

BACKGROUND OF THE INVENTION

There is a growing need for a home diagnostic system for monitoring various personal physical health conditions and for the early detection of health problems. Such systems are typically used to determine fertility periods, pregnancy, labor onset, alcohol levels, glucose levels of diabetic persons and indicators that signal a need for comprehensive HIV testing. Home diagnostics systems are desirable because they are convenient to use and reduce health care costs.

(1) Field of the Invention

The present invention relates to saliva-monitoring oral devices including saliva-monitoring electrical toothbrushes.

(2) Related Art

Several patents describe various systems for collecting and diagnosing the contents of saliva. Some of the prior art diagnostic purposes and collection and testing procedures are summarized below.

Fertility, Pregnancy and Labor Onset Tests

U.S. Pat. No. 3,968,011 by Manautou et al. shows the use of optical density curves of saliva samples to indicate pregnancy. Such curves have a first peak and a smaller second peak in daily measurements; however, the second peak is eliminated when pregnancy occurs. In application, a paper test strip impregnated with a peroxidase and guaiac shows a color change when wet with saliva during the fertile period. The change is caused by the presence of peroxide in the saliva. The test strip is costly and may not be reused. U.S. Pat. No. 4,385,125 by Preti et al. monitors saliva for the concentration of certain long-chain alcohols, particularly dodecanol, for detecting ovulation. The dodecanol content of saliva remains at a relatively constant level throughout the menstrual cycle, but exhibits a single peak at the time of ovulation. Because the method is complicated, it is more suitable for laboratory tests than home use. Several commercially available hand held devices predict ovulation based on a measured peak in electrical resistance corresponding to sodium and potassium electrolyte levels which are reflective of hormone changes that occur several days before ovulation. The measured data on the changes of electrolytes in saliva may be inconsistent since an oral sensor probe is placed on the tongue where the thickness of the saliva layer may vary. While there are disadvantages associated with all of the above methods, each method demonstrates the feasibility of using an optical sensor or a conductivity sensor for measuring signals derived from a saliva sample to predict an ovulation period or pregnancy.

U.S. Pat. No. 5,480,776 by Dullien discloses a method for detecting the onset of labor by analyzing a body fluid, such as saliva, for estriol hormone concentration. The method correlates the estriol concentration with a standard value and relates the rate of increase of the concentration as an indicator of the onset of labor. A preferred assay utilizes an enzyme-labeled component in a competitive binding assay for estriol. In a typical assay, antibody is attached to a solid surface such as a porous reagent strip. The antibody-coated solid surface is then contacted simultaneously with a sample and with a competitive binding compound. After reaction, if sufficient estriol is present in the sample, then no enzyme is present to produce a color change (positive result). Otherwise, a change of color indicates the absence of estriol in the sample (negative result). This method is most effective when the rate of increase of estriol hormone is monitored on a daily or regular basis.

Alcohol Tests

Saliva may also be used to test blood alcohol level. Ethyl alcohol is a component of the blood that perfuses the salivary glands. The ethanol content of saliva has been determined through measurements to be about 9% higher than capillary blood alcohol content. However, U.S. Pat. No. 5,968,746 to Schneider et al. indicates a high correlation coefficient (r=97) between ethanol concentrations in simultaneously drawn blood and saliva samples. The test unit described in the patent uses a vacuum-packed ampoule containing dried enzyme, a solution swellable plug and a suitable colorimetric reagent. Since the test is activated by breaking the ampoule, it is not re-useable and the test is not suitable for home use. The test strip method of U.S. Pat. No. 4,786,596 to Adams, uses alcohol oxidase, peroxidase and a hydrogen donor indicator such as tetraalkalbengidine in a carrier matrix supported on the strip. The alcohol oxidase functions as a catalyst to convert any ethanol present along with ambient oxygen to acetaldehyde and hydrogen peroxide. The peroxidase functions as a catalyst to induce a color change in the hydrogen donor indicator and converts the hydrogen peroxide to water. Because this method requires the use of a color chart to visually identify the alcohol concentration, it is subject to interpretation errors. The test procedure does, however, confirm the effectiveness of testing alcohol concentration by using saliva.

Blood Glucose Tests

Efforts have been made to develop a noninvasive monitoring procedure for blood glucose using a saliva sample instead of drawing a test blood sample from a finger. U.S. Pat. No. 6,102,872 by Doneen et al. discloses that glucose concentration of oral fluid is approximately 0.5% to 1.0% of the contemporaneous blood concentration. The patent details the correlation between measured oral glucose level and the concentration of blood glucose. The patentee uses a small pore size membrane having sodium citrate mixed with citric acid for stimulating saliva secretion and collecting filtered saliva. The filtered saliva is in contact with a colorimetric glucose film. The film contains the enzymes glucose oxidase and horseradish peroxidase, and a combination of dyes and accessory reagents, such as buffers and stabilizers, for producing a colored spot or line with color intensity proportional to the glucose concentration in the saliva sample. In application, reflectance measurements by a spectrophotometer are converted into an estimated blood glucose value with the use of a computational chip in a monitor.

U.S. Pat. No. 5,500,374 by Wenzhi uses a UV detector and electrostatic ion chromatography to produce a chromatogram from a saliva sample. Diagnosis for diabetes mellitus is based on the presence or absence of a chromato-peak of the diabetes mellitus-specific component. Since the saliva sample is required to be injected into a stationary phase in a separation column, the method is not suitable for home use. In U.S. Pat. No. 4,105,522 to Friedenberg et al., the concentration level of glucose in saliva is determined by oxidizing a test sample with an oxidizing agent and measuring the electrical potential (in millivolts) of a primary cell in which the residual oxidizing solution is the electrolyte. U.S. Pat. No. 5,264,103 by Hoshioka, U.S. Pat. No. 5,997,817 by Crismore et al. and U.S. Pat. No. 6,004,441 by Fuziwara et al. use a dry reagent layer of specific chemical compositions and a biosensor of a special electrode arrangement for testing glucose concentration. The dry reagent layer is dissolved in a blood sample. The biosensor is not renewable, i.e. it can not be regenerated for subsequent use.

HIV Tests

Saliva is also used to test for HIV indicators. Advantages of using saliva samples instead of blood test samples are avoidance of costly handling and reduction in health risks to workers. While HIV is not known to be transmitted in saliva, it is present in saliva. A published research article, "The Diagnostic Uses of Saliva," J. Oral Pathol. and Medicine, 19:119–125 (1990), suggests that saliva be used as a source for screening for anti-HIV antibodies. Furthermore, a commercial anti-HIV assay kit has been developed for the purpose of detecting anti-HIV antibodies in saliva. In U.S. Pat. No. 5,695,930 by Weinstein et al., a HIV test kit method for detecting anti-HIV-I antibodies in saliva is described. To enable confidentiality and convenience of frequent testing, the patent discloses an inexpensive assay kit for anti-HIV antibodies in saliva that can be personally performed at home without the need for a laboratory immunoassay. It uses an enzyme reporter molecule of alkaline phosphatase that promotes a reaction which is detected by a change in color of the reactants. The patent also describes a solid phase immunoassay for testing in three steps. The first step uses a test strip having nitrocellulose-bound proteins in direct contact with saliva for 30 minutes; the second and third steps involve incubating the test strip with goat anti-human IgG and with a NBT/X phos substrate, respectively. Test results show either a blue spot which indicates a positive test for anti-HIV antibodies in the saliva, or a white spot which indicates a negative test. Although this method involves repeated washing and incubation of a test strip, the feasibility of using saliva to test for HIV is promising for use in home diagnostic systems if test procedures are simplified and economized.

The foregoing patents demonstrate various procedures and equipment used for testing saliva for ovulation, pregnancy, labor onset, alcohol, glucose concentration, and HIV.

Sample Collection and Monitoring

The prior art has disclosed various means for collecting saliva samples. U.S. Pat. No. 4,834,110 by Richard describes a suction cup for collecting a saliva sample. Suction is applied to a person's cheek around the parotid salivary duct and a pulsing pressure or electrical stimulation is applied to promote the flow of saliva to a collector vessel. This method requires the soft rim of the cup to be in full contact with the cheek and with a partial vacuum pressure for suction. The device is for one-time use in laboratory testing. Another device that uses a collecting cup for monitoring saliva is disclosed in U.S. Pat. No. 6,061,586 by Kuperman et al. The device includes a sample kit and an electrode assembly for immersion within a patient's saliva. The sample kit is comprised of a syringe-like element with a piston and a sponge member for absorbing the saliva to be compressed by the piston into the collecting cup. The voltage signal is processed by a microprocessor according to a selected mathematical model. The disadvantages associated with using the kit are potential contamination of saliva by the sponge and the per use costs of the non-reusable disposable components. An in-situ testing procedure with direct contact between a non-saliva test fluid and sensors without utilization of a third medium for transporting or extraction is disclosed in U.S. Pat. No. 6,080,118 by Blythe. The insertable portion of a vaginal probe includes a number of fluid flow grooves and the probe is rotatable for stimulating the secretion of vaginal fluids for collection. The sensors are electronically coupled to integrated circuitry for analyzing measured data and are mounted on the surface of the vaginal probe to test a non-controlled quantity of test fluid between the sensors and the vaginal wall. The inconsistency of the volume of the test fluid can lead to significant measurement errors.

U.S. Pat. No. 5,684,296 by Hamblin describes a fiber optic liquid sensing system. The system uses a reflective-type optical sensor which has a housing with a highly polished reflector. The reflector is positioned at a distance opposed to the terminal surfaces of light emitting and a light receiving strands, which are bundled in side-by-side fashion. There are a number of apertures on the circumferential wall of the housing for drawing in a fluid sample for optical measurements. Although the sensor housing is compact and contains all the sensor components, the configuration of the apertures may entrap air inside the housing that causes measurement errors. Because the segmented walls between the apertures hinder thorough cleaning, the sensor is non-reusable.

U.S. Pat. No. 5,206,711 by Bethold et al uses an open channel in conjunction with a fluid opacity sensor for measuring opacity of a fluid sample in a process line. To compensate for light source drift caused by temperature effect and 60 Hz line noise in the processing electronics, a reference optical pathway having the same optical system is used and a signal processing means is provided to cancel the effects of the light source drift. The width of the channel used is designed for the passage of fluid rather than for inducing a capillary effect to draw in and hold a fixed volume of sample fluid for testing. U.S. Pat. No. 6,099,484 by Douglas et al. discloses a capillary tube for drawing body fluid from an incision and a test strip affixed to an upper end of the capillary tube for receiving the fluid. By pressing the device against the skin at the site of an incision, the test strip directly contacts body fluid emanating from the incision. To ensure that a sufficient sample size enters the tube, a drop-detecting mechanism uses either electrodes or an optical system for detecting the height of the sample drop. Similarly, U.S. Pat. No. 5,100,620 by Brenneman uses a capillary tube in conjunction with an exposed reagent pad to contact a test fluid. A vent passageway having a smaller diameter than the capillary tube is also used. Optical measurement begins as the optics system senses the start of a change in color of the reagent pad. Since both methods employ a capillary tube of small diameter (ranging from 0.01 to 0.03 inches), the fluid inside the tube cannot be washed out to clean it for repeated uses.

U.S. Pat. No. 5,851,838 by Vetter et al uses a planar capillary gap for transporting a sample fluid over the top of a diagnostic test carrier. To avoid false test results caused by continuous re-diffusion of analyte out of a test area while the test reaction is in progress, the patentee uses excess sample liquid to surround the test carrier. Since the capillary gap is not closed during testing, the test is subject to measurement errors. Although each of these patents demonstrates use of a capillary tube for transporting a fluid sample over a test strip for testing, the capillary channels and test strips are manually replaced for each use. This is inconvenient and costly for use in a home diagnostic device.

Sensors suitable for use in conjunction with small spaces such as capillary test channels, are known. U.S. Pat. No.

5,335,305 by Kosa discloses fabrication methods for installing fiber optical sensors in fiber bundles fabricated from fibers that are bent with small radii. U.S. Pat. No. 5,851,838 by Vetter et al., U.S. Pat. No. 5,997,817 by Crismore et al., and U.S. Pat. No. 6,058,934 by Sullivan show various electrode matrices arranged in planar configurations. Sullivan details the use of four terminals in which voltage measuring electrodes are separated from current carrying electrodes, enabling only a low current to be drawn from a sample. The arrangement confines the measured current to the sensor chamber, thereby preventing the conductivity sensor from interfering with other sensors in the test instrument. The patentee describes the advantage of using a planar configuration to simplify the manufacturing process and enhance efficient fluidics so that the cells can be filled and washed out with a minimal volume of reagent. The size of the chip may be, for example, approximately 0.12 by 0.12 inches and can be disposed in a flow cell receptacle in a sensor housing to form one wall of a fluid flow path on which fluid flows perpendicular to the parallel arrangement of the electrodes. The width and spacing of the electrodes are not critical, each typically being 0.005 inches. The Crismore et al patent discloses the use of palladium as the electrode surface because of its resistance to oxidization and its relatively low cost. The preferable distance between electrodes is about 1.2 mm and the exposed area of an electrode need not be entirely covered with a test reagent.

Electrodes can also be used to measure pH. U.S. Pat. No. 5,573,798 by Kato relates to a pH-measuring electrode having a sensor film of metal oxide which is sensitive to a hydrogen ion in solution. In operation, the pH-measuring electrode is immersed in the solution to be measured together with a reference electrode such as a calomel electrode or a silver-silver chloride electrode. Based on the potential difference between the two electrodes, a pH value is determined.

The combined use of an electrode matrix with a dry reagent layer for testing physiological fluids has been the subject of several patents on biosensors including U.S. Pat. No. 5,120,420 by Nankai et al., U.S. Pat. No. 5,264,103 by Yoshioka et al. and U.S. Pat. No. 6,004,441 by Fugiwara et al. Using blood drops as test samples for detecting glucose, the biosensors disclosed in these patents utilize an electrode matrix produced by screen-printing and a dry reagent layer containing an enzyme which reacts only to glucose in the blood sample. The enzyme contained in the reagent layer is dissolved in the sample liquid. According to the description contained in U.S. Pat. No. 6,004,441 by Fugiwarra et al, the electrode system of a biosensor is comprised of an electrode for measurement and a counter-electrode which functions as a reference electrode. The covering on top of the electrode matrix is a reagent layer which includes glucose oxidase as an enzyme and potassium ferricyanide as a mediator. When a voltage is applied between the electrodes, electric current flows in proportion to the concentration of glucose. Typical dimensions of an electrode matrix are 5 to 10 nm in electrode thickness and about 70 .mu.m between electrodes. For better performance, the width of each of the two counter-electrodes is preferably the same or larger than that of the measuring electrode. In operation, a drop of blood is placed on the reagent layer after the electrode system is energized. After the change in conductivity stabilizes, the voltage applied is suspended for a period of time to allow for the oxidation of glucose and the reduction of potassium ferricyanide to take place. After completion of the reaction, a voltage is applied again to cause oxidation of the reduced potassium ferricyanide. This results in an electric current which is proportional to the concentration of glucose, a measurement of the blood sugar level. The reagent layer is not reusable.

U.S. Pat. No. 5,208,147 by Kagenow et al. discloses a method for using a discardable measuring device and a conditioning fluid chamber for repeated release of fresh conditioning fluid for calibrating a sensor for measurements. However, the device requires the inconvenient step of moving the sensor to a conditioning fluid chamber to expose the sensor surface to the conditioning fluid.

In summary, there have been a significant number of patents which utilize saliva samples to test for fertility periods, pregnancy, labor onset, alcohol concentration, glucose concentration and HIV indicators. While various articles such as "What's Next: Medicine" (Popular Science, July 2000, pp 50–54) discuss the need for home diagnostic devices, none is capable of performing the stimulation and collection of saliva and testing the saliva sample in an all-in-one handheld device for economic, efficient and convenient repeated regular uses at home.

It is therefore an object of this invention to provide a portable handheld diagnostic oral device which stimulates saliva production and collects saliva samples in a test channel. It is another object of the invention to test saliva samples for the purpose of monitoring selected biophysical conditions of a user on a daily basis. It is a further object of the invention to provide a portable hand held diagnostic device which has a toothbrush component.

SUMMARY OF INVENTION

These and other objects of the invention are accomplished with a saliva-monitoring oral device which is inserted into the mouth to collect and test saliva. As an all-in-one, handheld diagnostic device, it stimulates saliva production and collects it in a test channel where measurements are conducted by sensors. Measured data is stored and analyzed for abnormalities by a microprocessor included in the handle of the device. During testing, various kinds of reagents may be used depending on the type of test (fertility, pregnancy, labor onset, alcohol content, glucose concentration, HIV indicators, etc.) being conducted. Each reagent is stored in a replaceable cartridge which is inserted into the handle for use in a particular test.

The preferred embodiment of the oral device is configured as a saliva-monitoring, biosensor electrical toothbrush which has a handle and a brush head. The handle contains a battery, microprocessor, motor, a rotatable and slideable driveshaft and a reservoir for storing reagent used in testing saliva. A plurality of bristles which rotate or oscillate are attached to the top of the brush head and a notch-like open channel traverses the width of the bottom of the brush head. Sensors are mounted on the walls of the test channel and a small vent groove is positioned at the bottom of the channel. A conduit with one-way check valves connects the reagent reservoir to an inlet opening in a wall of the test channel. The channel has a cover to seal it closed while testing is in progress. A display unit for the microprocessor is attached to the handle.

In operation, a switch is turned on to start the oscillation of the bristle elements. This also causes vibration of the brush head and the open test channel. When placed in contact with the tongue or cheek, the vibrating channel walls stimulate the secretion and accumulation of saliva under the tongue or elsewhere in the mouth. Saliva is drawn into the open channel by its capillary action, facilitated by a partial vacuum caused by the vibration of the channel walls. The complete filling of the open channel is detected by a sensor which is positioned at the inner most location of the open channel. At the moment of complete filling, the control system activates a solenoid which causes its actuator disk to press on an internal elastic pump button which dispenses a controlled amount of reagent into the test channel. Simultaneously, the solenoid's actuator rod pushes the slideable drive shaft forward which causes a channel cover that is mechanically linked to the drive shaft, to close the open channel. The synchronization of the reagent dispensing and the channel closing is timed to keep the dispensed reagent inside the test channel. During these actions, the continued vibration of the channel accelerates the mixing of the reagent with the saliva sample. After a predetermined mixing time period, the sensors take readings on the optical density and/or the electrical current level which reflect the concentrations of targeted analytes of the saliva sample. The microprocessor inside the toothbrush handle compares newly measured data against established trend and threshold values to signal abnormality. The display unit is capable of providing trend data and sending acoustical or visual warning signals. The saliva collection and testing steps are usually completed within 30 seconds. After the display of the test results, the control system deactivates the solenoid to retract the actuator rod which brings the channel cover to the open or home position. After the test channel is cleansed, the toothbrush is ready to be used for brushing in the normal manner.

BRIEF DESCRIPTION OF THE DRAWINGS

FIG. 1a is a cross section view of a saliva-monitoring electrical toothbrush.

FIG. 1b is an enlarged cross section view of the brush head shown in FIG. 1a.

FIG. 2a is a cross section view along B—B of FIG. 2f showing a reagent dispensing mechanism.

FIG. 2b is a cross section view along A—A of FIG. 2a showing a test channel, reagent dispensing opening and two optical sensors.

FIG. 2c is a partial enlarged view of FIG. 2b.

FIG. 2d is a cross section view along B—B of FIG. 2c.

FIG. 2f is a plan view of a saliva-monitoring electrical toothbrush.

FIG. 3a is a perspective view of a channel cover.

FIG. 3b is a cross section view showing a spring-loaded drive shaft in a brush head for mounting the channel cover of FIG. 3a.

FIG. 3c is a side elevation view of a brush head with the brush elements removed showing mounting slots for a channel cover.

FIG. 3d is a side elevation view of a brush head with a channel cover and a snap-on bracket for holding bristle elements.

FIG. 3e is a cross section view of a drive shaft mechanism and corresponding channel cover engagement at the open position.

FIG. 3f is a cross section view of a drive shaft mechanism and corresponding channel cover engagement at the closed position.

FIG. 5i is a flow chart of the sequential process steps in the operation of the toothbrush.

FIG. 6a is a section view of saliva-monitoring toothbrush which stores and dispenses dentifrice material.

FIG. 6b is a partial enlarged view of the brush head of the toothbrush of FIG. 6a.

FIG. 9a is a perspective view of a brush head which has an open channel matrix positioned on a side surface of a brush head.

FIG. 9b is a cross section view along A—A of FIG. 9a.

FIG. 9c is an enlarged view of the open test channel matrix of FIG. 9b.

FIG. 10b is a cross section view along A—A of FIG. 10a.

FIG. 11a is a cross-section view of a brush head having a hydrophobic channel wall.

FIG. 11b is a cross-section view along A—A of FIG. 11a.

FIG. 11c is a top view of FIG. 11a.

DETAILED DESCRIPTION OF THE INVENTION

Figures 1C, 1E:
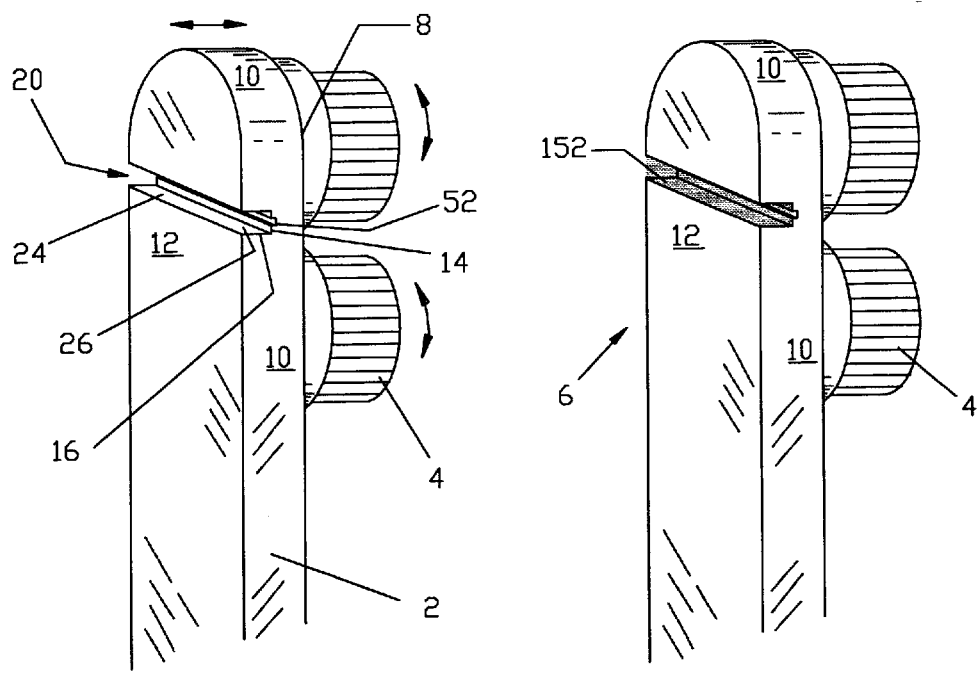
FIG. 1c is a perspective view of the brush head shown in FIG. 1b with an empty test channel.
FIG. 1e is a perspective view of the brush head shown in FIG. 1b with a saliva sample in the test channel.

FIGS. 1a, b, and c show an electrical toothbrush having handle 2, brush head 6 and bristles 4. The brush head has top surface 8, side surface 10 and bottom surface 12. Open test channel 20 is recessed in bottom surface 12 and traverses the width of brush head 6. The open test channel has an upper wall 18 and a lower wall 16 as well as a base 14, all of which form a front opening 24 which is opposed to base 14. Test channel 20 also has two side openings 26 which are opposed to each other on the side surfaces 10 of the brush head. The channel gap between the upper and the lower walls is defined by front opening 24 and side opening 26. It is optimally designed with a width narrow enough for inducing capillary flow and for holding saliva within the open channel but sufficiently wide to allow for the passage of cleaning water to flush out saliva inside the test channel. Vent groove 52 is situated along the length of the channel base 14. The width of the vent groove is sufficient to vent entrapped air during filling of the test channel with saliva but is too narrow for saliva or water to penetrate into the groove. As shown in FIG. 1b, a sensor pair consisting of light emitter 36 and light detector 50 is positioned across the opposing walls of the test channel. The detection surfaces of the sensor pair are nearly flush with the surfaces of the upper and lower walls to facilitate cleaning. Leads 38 connect the sensor and microprocessor 34.

Figure 1D:
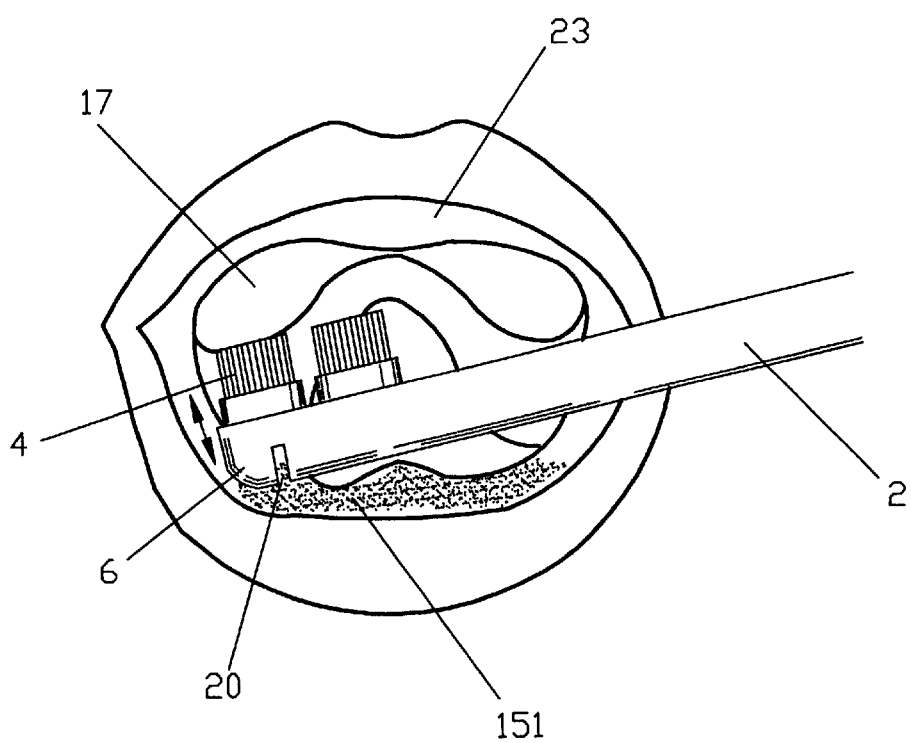
FIG. 1d is a side elevation view of a saliva-monitoring electrical toothbrush positioned under the tongue of a user's mouth for saliva collection.

Vibration of the brush head stimulates production of saliva by the salivary glands. Biased disk 40 and off-centered rod 44, which are mounted on drive shaft 32, impart a vibrating motion to brush head 6. Drive shaft 32, which is driven by a motor 30, also causes oscillation of the bristle elements 4. FIG. 1d shows the collection of saliva by brush head 6, which is placed in a mouth 23 under tongue 17 with the open channel 20 in contact with saliva pool 151. In operation, the vibration of the brush head generates a low pressure or partial vacuum condition in the vicinity of the open test channel. When immersed in a pool of saliva, the low-pressure zone immediately next to the open channel induces saliva to flow into the open channel. The saliva flow pushes air out or forces entrapped air into vent groove 52 to release it from the open channel. After the vibration ceases, the brush head is removed from the saliva pool. The surface tension and the viscosity of the saliva retain the saliva 152 inside the narrow open channel as shown in FIG. 1e. The gap across the channel between the sensor pair is filled thereby forming a continuous saliva medium for sensor measurement.

The sensor pair is typically either an optical fiber sensor or a color responsive electrical conductivity sensor. An optical sensor, either a transmittance or reflective type, is used to measure the opacity or colorimetric response of the saliva. The light emitter and the light detector of a transmittance type optical sensor are positioned on opposing walls of the test channel. The reflective type sensor has a light emitter strand and a light detector strand aligned side-by-side in a housing that is mounted on the lower channel wall (see FIGS. 5f and 5g). Similarly, in the case of a conductivity sensor, an electrode and a counter electrode are positioned across the channel gap to measure the current level of the saliva corresponding to the concentration of an analyte. In a preferred embodiment, two sensor pairs are used which can be the same or mixed. The first sensor pair is located close to front opening 24 for early detection and measurement of saliva, and the second sensor pair is located close to base 14 to detect when the channel is completely filled. Complete filling of the test channel is automatically determined as the readings of the second sensor pair start to exceed a predetermined threshold value which is indicative of the complete filling of the gap between the opposing measuring elements of the second sensor pair. This threshold value is established after repeated regular filling of the test channel by a user. The threshold value for the second sensor is the same as the first sensor if they are the same kind of sensor. If different kinds of sensors are used, then each kind has its own threshold value.

Microprocessor 34 controls the timing of the vibration of the brush head, the activation of the sensors and the analysis of the output signal from the sensors. The sensors are activated at the same time as the brush head vibrates for monitoring the filling of the test channel by the inflow of saliva. When the second sensor detects the moment of complete filling of the test channel, the readings of both the first and the second sensors are considered valid signals and are stored in the memory of the microprocessor for analysis. Trend data from the analysis is charted in standard display format. An example of trend data is provided in U.S. Pat. No. 3,968,011 by Manautou et al., which shows the peak of optical density of a saliva sample two days before menstruation. Using measured data such as that illustrated in the Manautou patent, an algorithm in the microprocessor recognizes the peak and compares the maximum value with an established threshold value. The measured data also is displayed on an LED board to indicate normal data trend and peaks of optical density. If the peak of the displayed data is out of normal range, an acoustic or visual indicator signal is activated to alert the user. To increase the reliability of measured data, two sensors 78 of the same kind are placed near the entrance of a test channel which has a reagent dispensing opening 86 as shown in FIG. 2b. These sensors are used for cross checking measured data to analyze the consistency and quality of saliva collection. The saliva measurements are preferably taken prior to brushing at the same time each day. To adjust for possible effects of saliva residue in the test channel and sensor signal drifts in the system, the sensor readings are taken automatically prior to the collection of a saliva sample for calibration purposes. This minimizes or eliminates measurement errors.

Figure 2E:
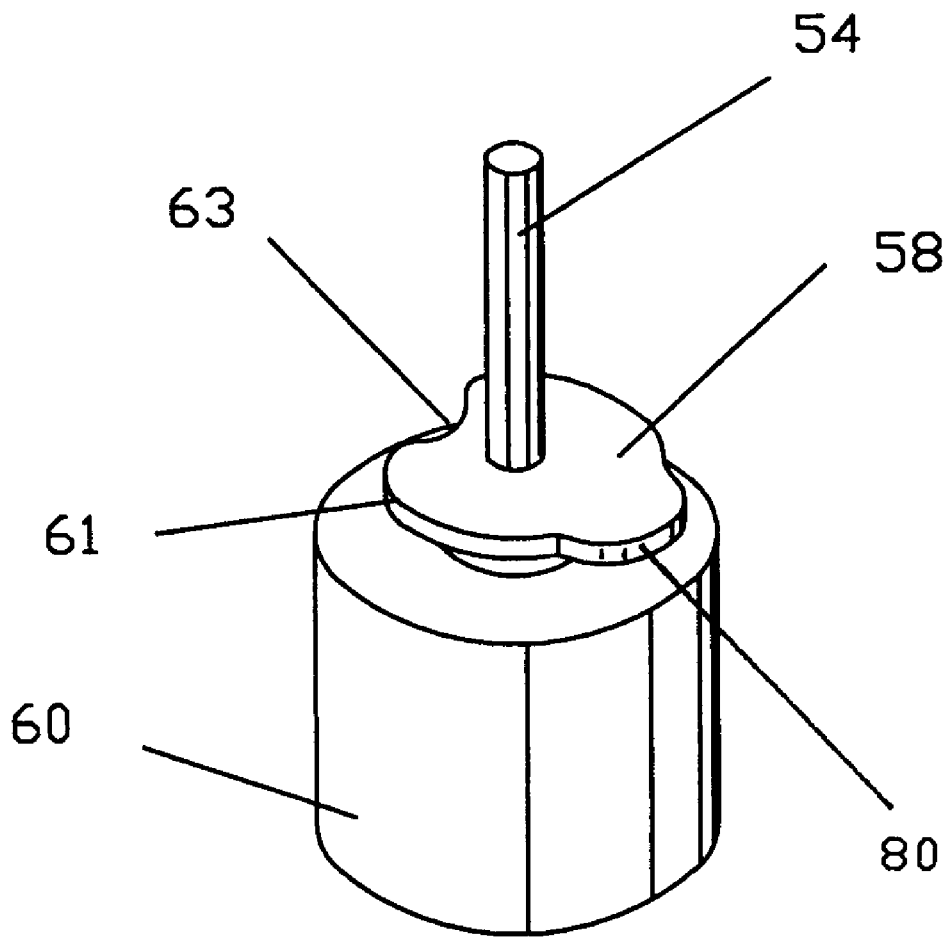
FIG. 2e is a perspective view of a solenoid assembly.

For diagnosis of saliva that requires the use of a reagent for measuring an analyte such as glucose, the toothbrush includes a reagent-dispensing feature. FIG. 2a shows an electrical toothbrush having a test channel in which a first one-way check valve 66 is positioned between two sensors 78 on top of reagent dispensing opening 86 at the end of reagent flow channel 74. Further illustrations of the first check valve and the flow channel are shown in FIGS. 2b, 2c, 2d and 2e. Flow channel 74 is positioned inside of handle 2 which also houses battery 28, microprocessor 34 and the drive system of the electrical toothbrush.

The overall dispensing mechanism is similar to a that of a dentifrice dispensing toothbrush having a refillable cartridge and using an elastic actuator for pumping dentifrice as described in U.S. Pat. No. 5,909,977 by Kuo. For pumping the reagent, an elastic button 67 having a convex shape and made of resilient rubber is positioned near the exit of a second one-way check valve 71 which is mounted on top of an output opening of refillable cartridge 68. The elastic button is depressed by the forward movement of solenoid disk actuator 58 which is mounted on the solenoid rod 54 of the linear solenoid 60. Edge 61 of disk actuator 58 (FIG. 2e) is in interference position in the path of the forward stroke of actuator disk 58 against the elastic actuator button 67. The elastic button 67 is restored to its original shape as the disk actuator 58 is retracted from the forward position. In operation, the solenoid 60, activated by the microprocessor, moves actuator rod 54 and disk 58 forward so as to depress the elastic button 67. The depressed elastic button applies a hydraulic pressure to the reagent medium in flow channel 70 that keeps the second check valve 71 at a closed position while at the same time forcing a controlled quantity of reagent from flow channel 70 to test channel 20 through opening 86 on the channel wall. The reagent flow forces the first check valve 66 to open and remain at an open position during the dispensing action. At the end of dispensing, the retraction movement of the solenoid actuator releases the elastic button from the depressed position. Due to the requirement of the continuity of flow medium, the resilient recovery of the elastic button to its original shape causes back flow to the cavity under the elastic button. The vacuum force created by the back flow causes the opening of the second check valve 71 and the forward movement of the reagent of the same quantity to flow channel 70 from cartridge 68 which has a follower disk 69 exposed to the atmospheric pressure. During this back flow, the first check valve 66 is at the closed position under atmospheric pressure. The dispensing mechanism automatically dispenses a controlled quantity of reagent with repeated reliability.

The automatic reagent-dispensing feature may be disabled to provide for a non-automatic operation. FIG. 2e shows notch 63 positioned next to edge 61 of disk actuator 58, which is used to depress the elastic button when in the automatic dispensing mode. The profile of the notch is designed to avoid contact with the elastic button 67 even when the disk actuator 58 is moved forward with the solenoid actuator rod 54. The non-dispensing mode is enabled by rotating lever 80 on the opposite side of the disk actuator 58 to a different angle. The lever is accessible through a lever slot 81 in the housing as shown in FIG. 2f. Lever slot 81 has two small indents 83 for lodging the lever 80 which is biased against the indents for anchoring. This non-dispensing mode is used when the toothbrush is used for more frequent brushings in a day at times when saliva monitoring is not necessary.

The required quantity of reagent dispensed into the test channel depends on the volume of the test channel, analyte to be measured as well as the concentration and the clinical/chemical/diagnostic characteristics of the reagent. As measured data depends on the mixing ratio of the reagent and the saliva in the test channel, maintaining the volume of saliva inside the test channel is critical for gaining reliable measured data. To ensure no leakage of saliva from the test channel during the vibration of the brush head, a channel cover is used to seal the test channel openings. FIGS. 3a, 3b, 3c and 3d show a channel cover and mounting features on a brush head for sliding the channel cover closed to seal the test channel. FIG. 3a shows a saddle-shaped channel cover 88 having an inlet opening 90 which has the same configuration as that of the test channel opening. The channel cover has a pair of opposing half-circle-shaped ribs 94 for mounting on drive shaft 106 between a first thrust bearing 102 and a second thrust bearing 104 located within the toothbrush as shown in FIG. 3b. The mounting is accomplished by insertion of ribs 94 through corresponding slot openings 107 on the two sidewalls of the brush head as shown in FIG. 3c. An additional pair of guide ribs 92 is provided for engaging with the slots 97 on the sidewalls of the brush head as shown in the same figure. The channel cover is spring-loaded and biased toward the home or open position where cover opening 90 coincides with the opening of the test channel as shown in FIG. 3d. The biased condition is enabled by pre-compression of spring 100 by first thrust bearing 102 against bushing 103 that is fixed to or an integral part of the handle housing. The length of slots 97 and 107 enables sliding of the channel cover to a closed position where the inlet opening 90 is offset from the channel front opening 24.

The translation movement of the drive shaft controls the sliding action of the channel cover. As also shown in FIG. 2a, drive shaft 64 has a D-shaped bottom end 65 that is inserted into a hollow armature shaft 57 of motor 55, which has a rotatable core 56 and an outer stator 59. D-shaped bottom end 65 is pushed by the solenoid actuator rod 54, which is slidable inside the hollow armature shaft 57. FIG. 3e shows the alignment of the channel cover at its home position with respect to its mounting features on the brush head. When the solenoid 60 is activated, the solenoid rod 54 is extended so as to push the drive shaft 64 to the forward position. Second bearing 104 pushes the channel cover 88 to the closed position where spring 100 is under full compression. At the same time, disk actuator 58 depresses elastic button 67 which causes the dispensing of reagent to the test channel. FIG. 3f shows the channel cover at the closed position which seals the opening of the test channel. After a period of mixing assisted by the vibration of the test channel, and the acquisition of measured data, the solenoid actuator rod 54 retracts at the command of the microprocessor. The retracted actuator rod 54 causes the backward movement of the drive shaft 64 as the load on the spring 100 is being released. Accordingly, the channel cover is pulled back to its home position again by its linkage with the drive shaft through thrust bearings 102 and 104.

Figure 4A:
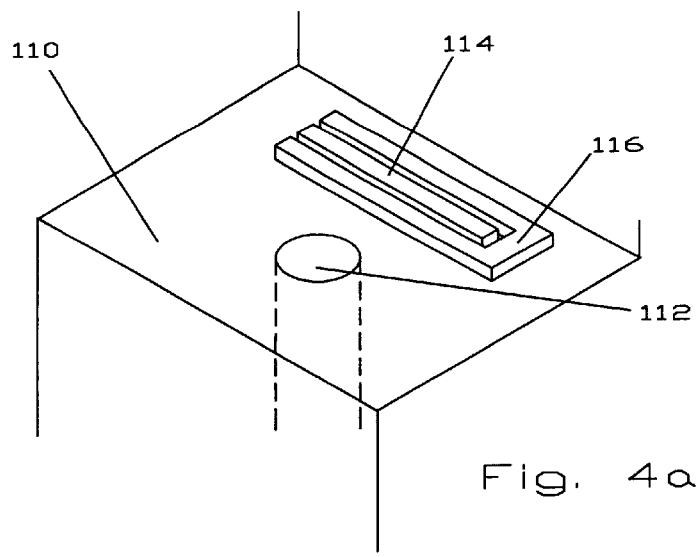
FIGS. 4a, 4b, 4c, 4d, 4e and 4f are perspective views of a renewable biosensor system with various parts of an electrode matrix positioned in a test channel.
Figure 4B:
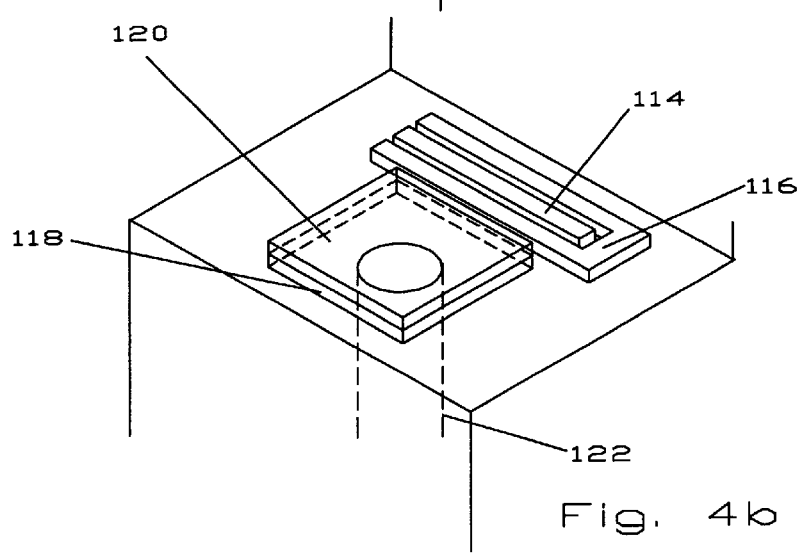
Figure 4C:
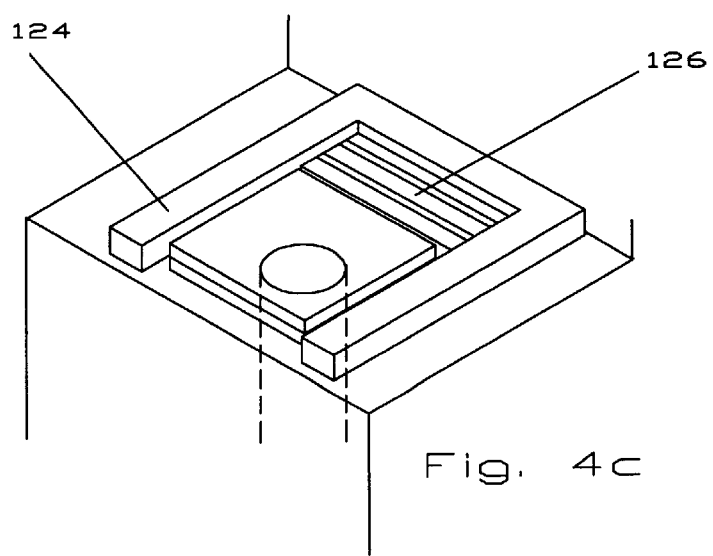
Figure 4D:
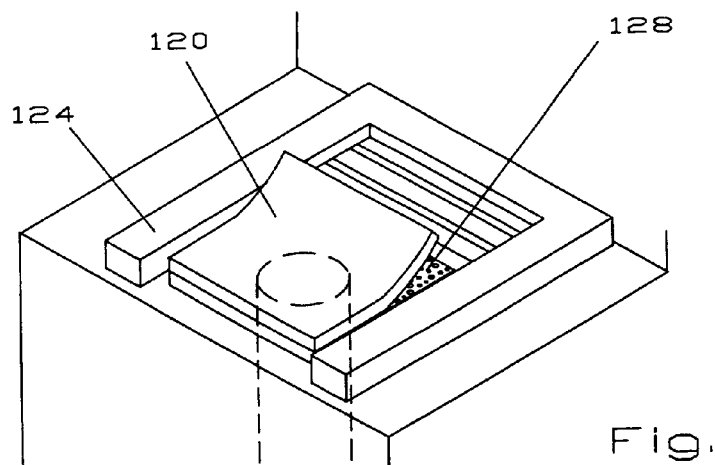
Figure 4E:
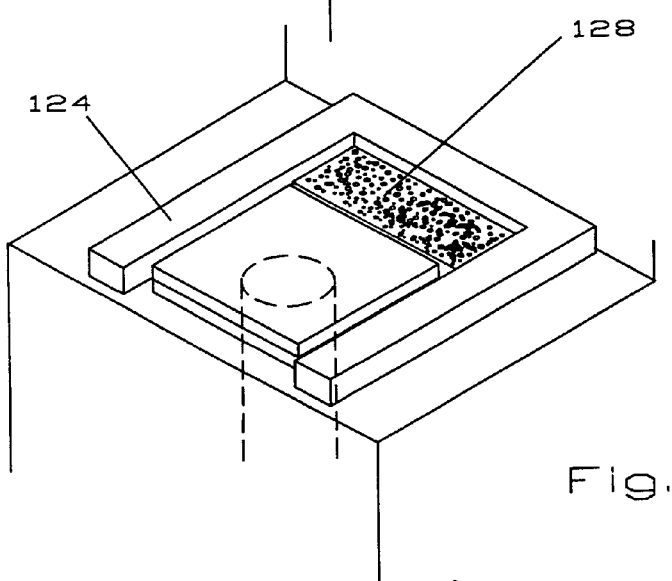
Figure 4F:
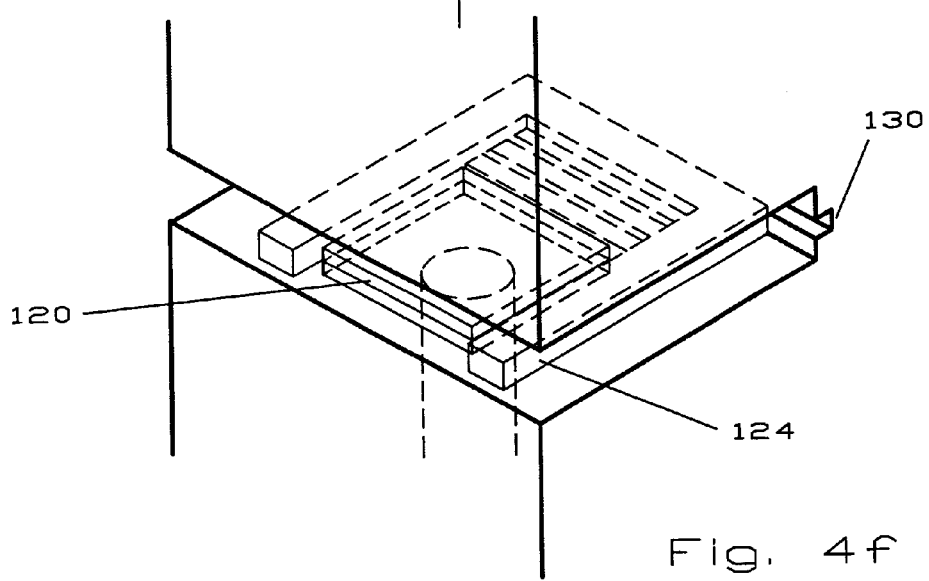

In other applications using a reagent, a biosensor is used to monitor an analyte in saliva such as glucose. FIGS. 4a through 4f show components of a renewable biosensor assembly which is a re-useable conductivity sensor incorporated into the test channel. The renewable biosensor comprises an electrode system, a reagent dispensing opening 112 and a one-way check valve 120, all positioned on the test channel wall. The electrode system consists of a matrix of electrode 114 and counter electrode 116, which are partially covered by insulation layer 124. The insulation layer as shown in FIG. 4c has a pattern of guide walls surrounding the edges of the electrode system and the edge of the check valve for confining the flow of the reagent. The check valve 120 as shown in FIG. 4d, is a resilient plastic film which is fastened at one end as a hinge and the opposite end is openable by a forced reagent flow. The check valve 120 is oriented to open toward the exposed area of the electrode matrix. FIG. 4e shows a reagent layer 128 deposited on top of the exposed electrode matrix as the flow of reagent settles at the end of dispensing action and the check valve 120 returns to its original closed position. A predetermined quantity of reagent is consistently dispensed by automatic means so that the thickness of the reagent layer is also consistently formed. In application, the renewable biosensor is incorporated in a test channel having a built-in vent groove 130 for releasing entrapped air as shown in FIG. 4f.

Figure 5A:
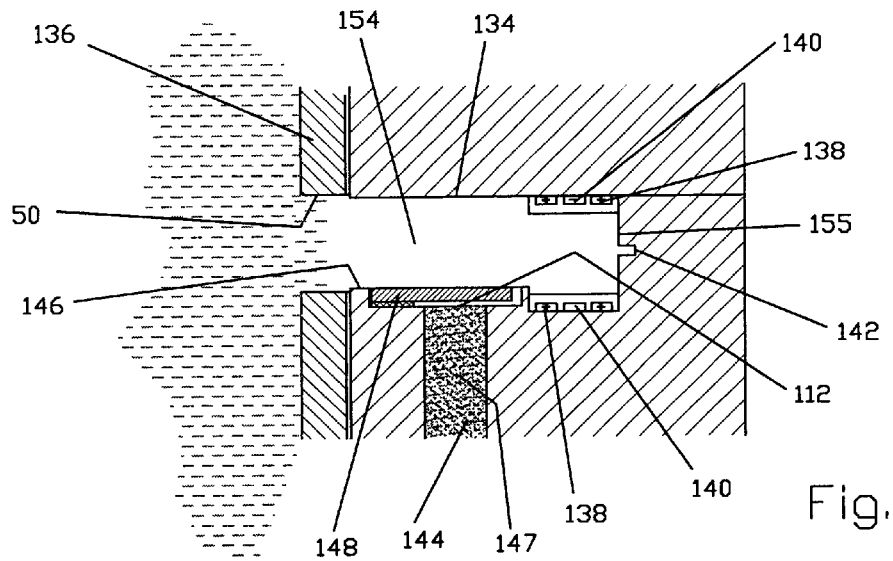
FIGS. 5a, 5b, 5c, 5d and 5e are section views of a renewable dual biosensor system with its test channel in sequential stages of operation during testing of a saliva sample.

The renewable biosensor is in planar form and requires two sensors for detecting the complete filling of the test channel. FIG. 5a shows two electrode systems with electrodes and counter electrodes, 138 and 140, of the same kind positioned on upper and lower walls 134 and 146, across the gap near the base 155 of a test channel 154 and opposing each other. As the reagent is only dispensed to the electrode system positioned on the lower channel wall 146 next to the dispensing opening 112, the reagent 147 needs to be mixed with the saliva 152 inside the test channel to provide a uniform mixture to be measured by both biosensors and for the measurements to be consistent. The consistency of measured data by the two biosensors at the same time is an indication of the complete filling of the test channel. Since the vibration of the test channel accelerates the mixing of the reagent and the saliva, the test channel is closed by the channel cover 136 during the vibration to prevent saliva from splashing out of the test channel.

Figure 5B:
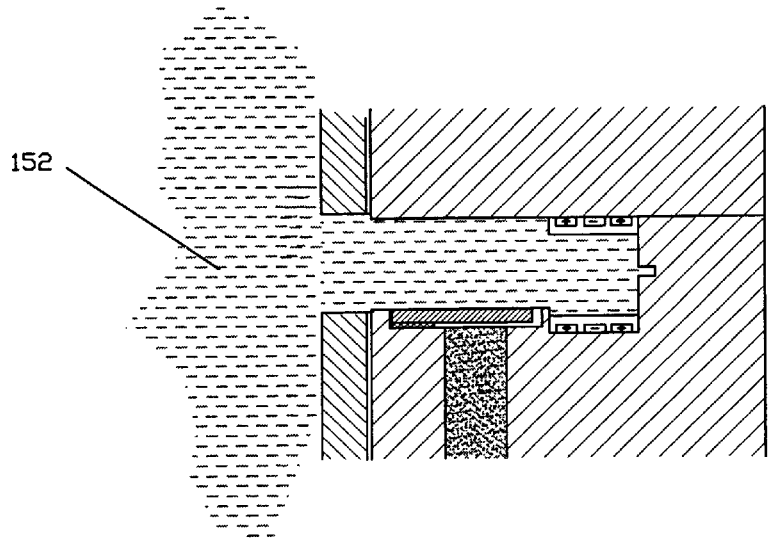
Figure 5C:
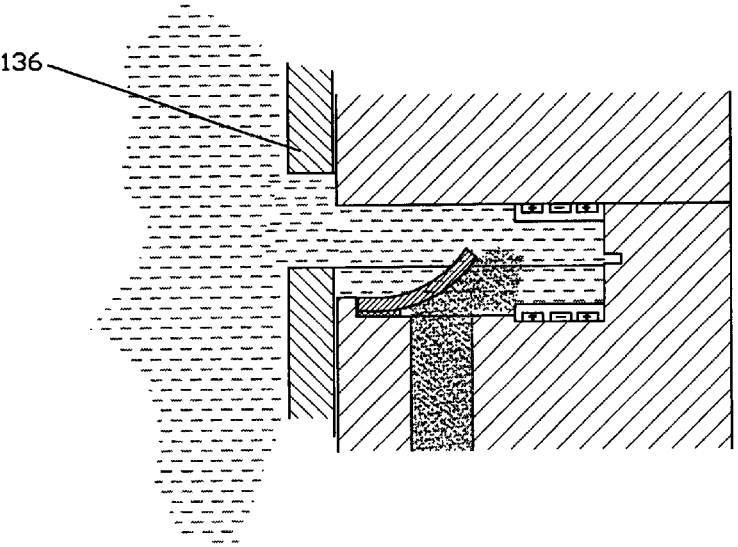

FIGS. 5a, 5b, 5c and 5d illustrate a sequence involving the actuation of a channel cover with the reagent dispensing and the measurement with a renewable biosensor. FIG. 5a shows the beginning of the intake of the saliva into the test channel 154 which is immersed in a saliva pool and in vibration mode with the brush head. The vibration results in lower partial vacuum pressure in the immediate vicinity of the channel opening that, in addition to the capillary effect, induces saliva to flow into the test channel. During this filling process, channel cover 136 is at the open position until the test channel is completely filled with saliva 152 as shown in FIG. 5b. The timing of complete filling is signaled by the microprocessor, which compares measured data from the two biosensors with predetermined threshold values and acceptable error ranges. At the moment of complete filling, the drive shaft is commanded to move forward. This causes the dispensing of the reagent and the closing of the channel cover. FIG. 5c shows the simultaneous actions of dispensing and partial channel closing. The channel cover may be closed before or after reagent is dispensed into the test channel, depending on the selected time delay and on the positioning of the cover and disk actuator 58 in relation to drive shaft 64 shown in FIGS. 3e and 3f. The timing control of channel closing is optimized to prevent diffusion of the reagent outside the test channel. Following closing of the channel, continuous vibration and mixing for a predetermined time period of a few seconds results in a well mixed solution for conductivity measurements by the two biosensors.

Figure 5D:
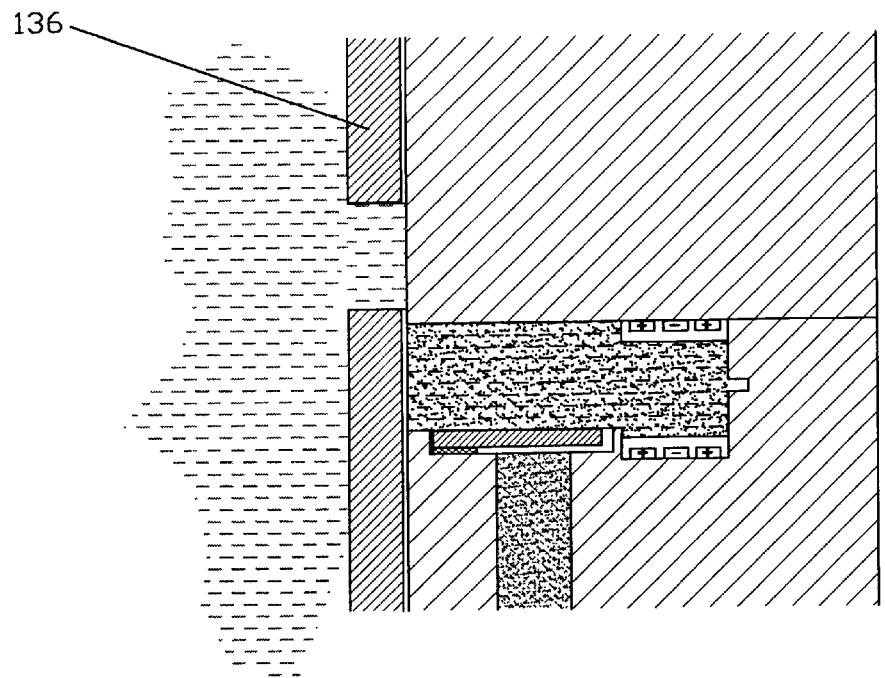
Figure 5E:
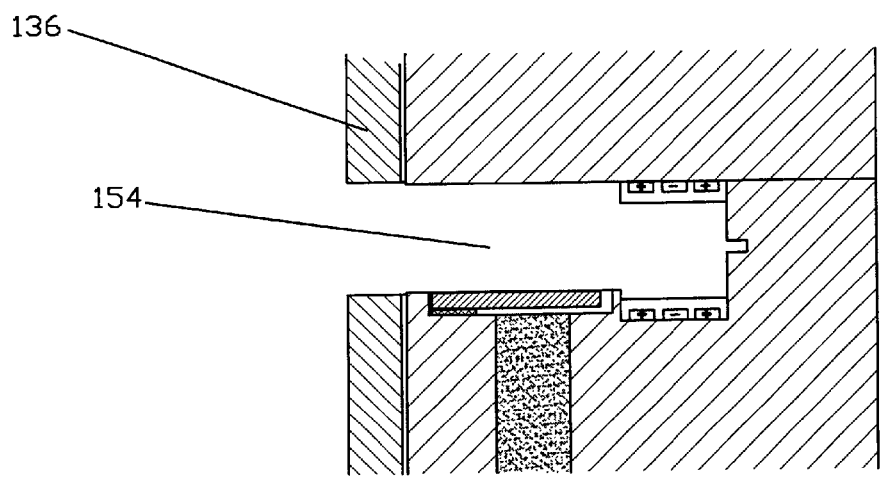

FIG. 5d shows channel cover 136 at the fully closed position at the end of mixing of the reagent and the saliva sample. After measured data is transmitted to the microprocessor for analysis and for generating output signals, the test channel is opened by returning the channel cover to its home position, which is achieved by retraction of the solenoid rod. The opened test channel is thus ready for cleaning by using tap water to flush out the mixed test solution. In the meantime, the retraction of the solenoid actuator rod 54 and the actuator disk 58 releases the elastic button 67 shown in FIG. 2a. The rebound of the elastic button to its normal position causes reagent to flow from the cartridge into the cavity under the elastic button. However, there is no backflow of reagent from the flow channel into the cavity because of the viscous resistance caused by the relatively long and narrow configuration of the flow channel. No residual mixed test solution and no cleaning water enter the dispensing opening at the time that the resilient second check valve 71 (see FIG. 2a) is also closing on the top of the dispensing opening. Consequently, a cleaned test channel 154 is ready for re-use since the used reagent layer has been washed out and the exposed electrode matrix is renewed. FIG. 5e shows a renewed test channel which is ready for the next testing cycle with fresh saliva.

The saliva measuring, monitoring and cleaning cycle normally takes less than 30 seconds, whereas normal brushing time requires about three to five minutes. When the toothbrush of this invention is not in use, it may be stored in an upright position with the test channel open for ventilation and drying. For storage in a prone position, the open channel may optionally be closed by a slidable plug attached to a toothbrush cover. A plug which is similar to that of the dentifrice-dispensing toothbrush described in U.S. Pat. No. 5,909,977 by Kuo is particularly suitable.

Figure 5G:
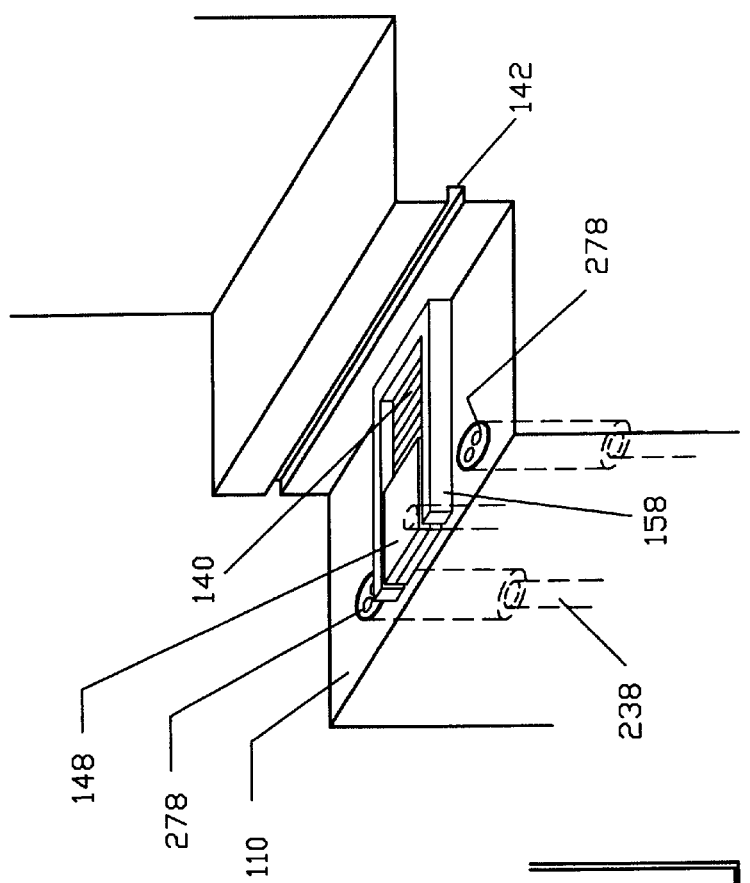
FIG. 5g is a perspective view of the test channel of FIG. 5f with the detachable wall removed
Figure 5F:
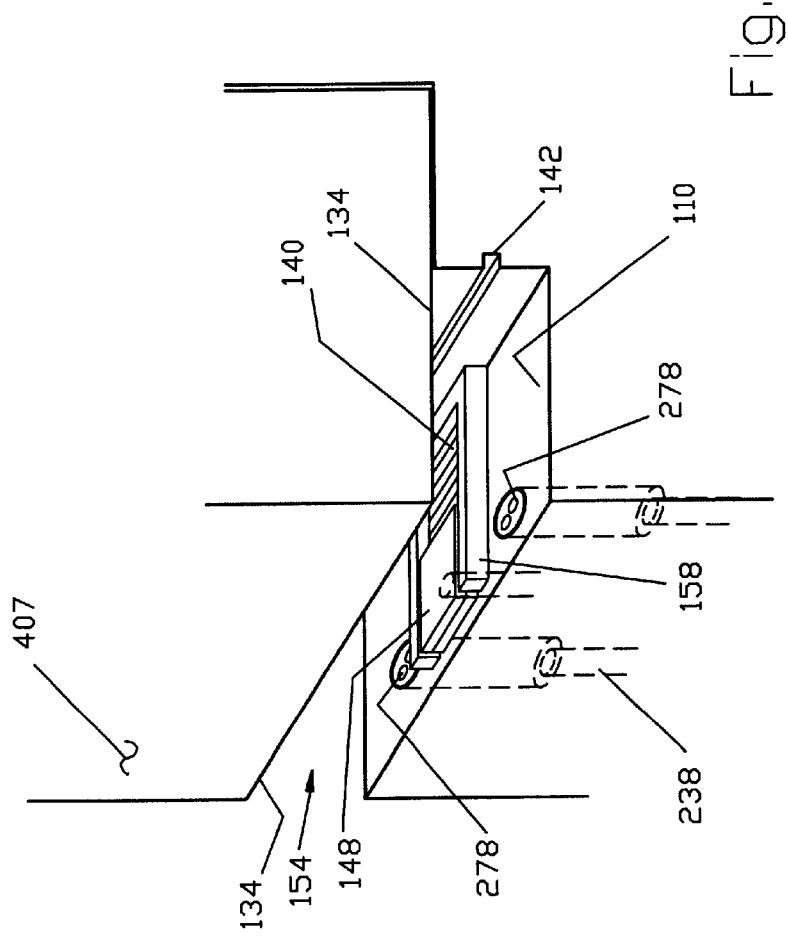
FIG. 5f is a perspective view of a test channel having a renewable biosensor, optical sensors and a detachable channel wall with an electrode matrix and two pairs of optical sensors.
Figure 8B:
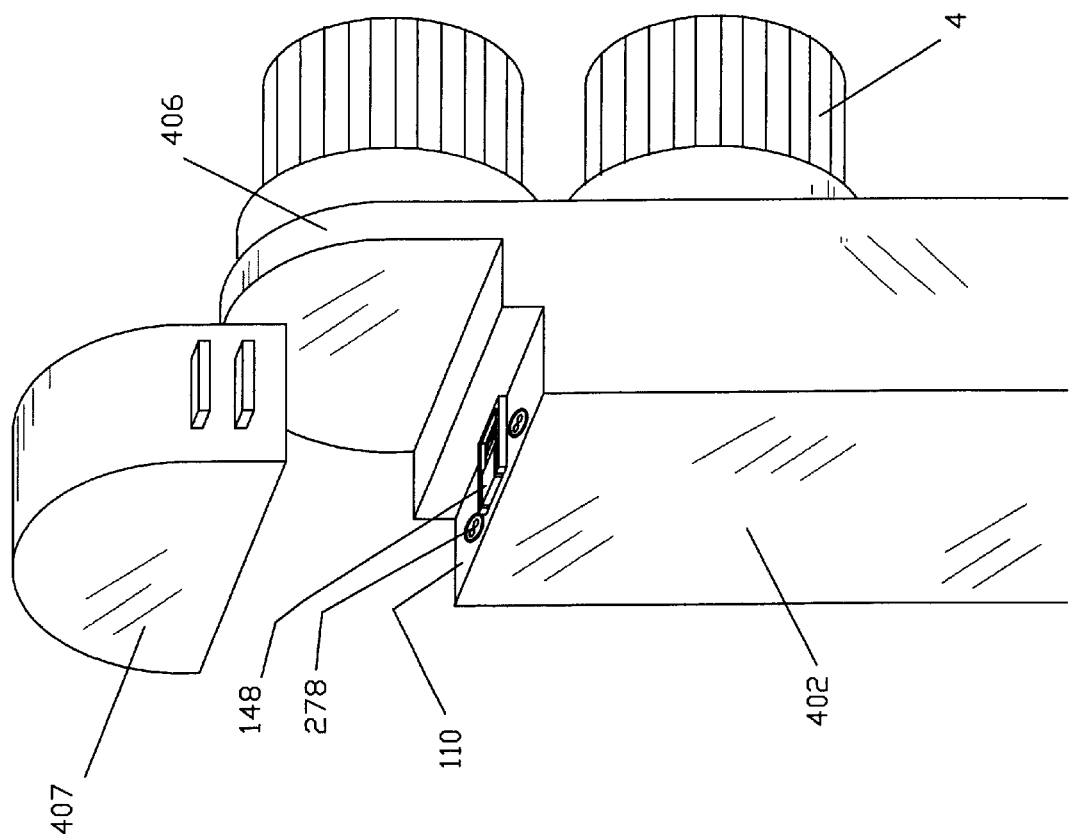
FIG. 8b is a perspective view of the brush head of FIG. 8a with the channel wall detached.
Figure 8A:
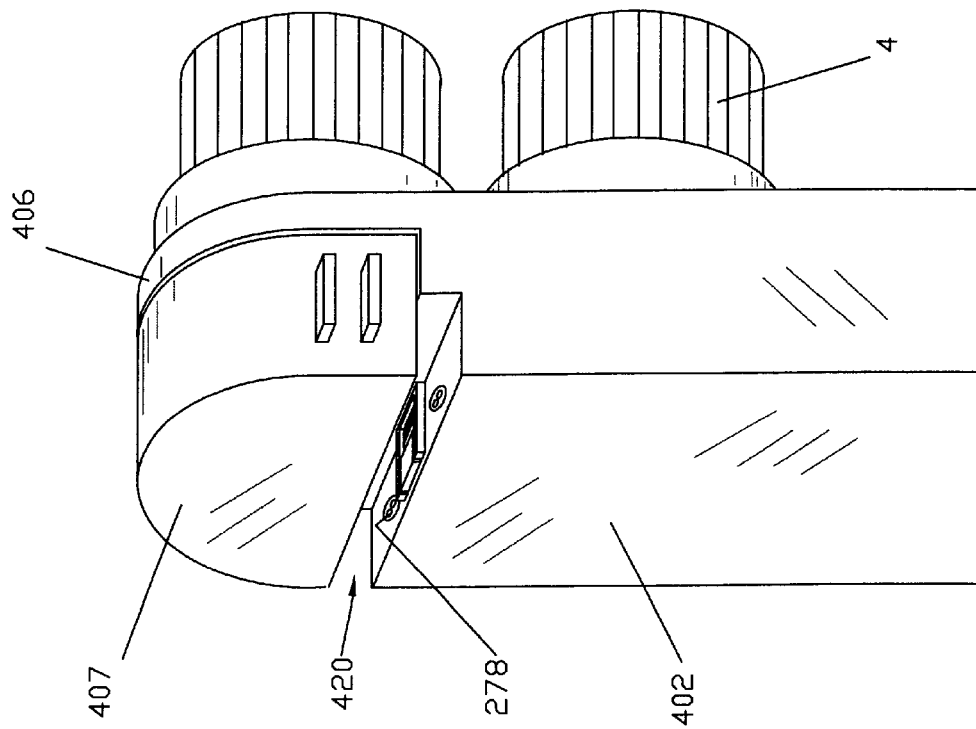
FIG. 8a is a perspective view of a brush head which has a test channel equipped with sensors and a detachable channel wall..

After repeated testing and cleaning of the test channel with tap water, the optical sensors and the biosensor in the test channel become contaminated with residual saliva mixture. In order to thoroughly clean the channel after prolonged repeated use, the upper wall of the test channel is optionally detachable. FIG. 5f shows the mounting of a detachable upper wall assembly 407 having upper wall 134 of test channel 154, which is equipped on lower wall 110 with reflective optical sensors 278 and electrode sensor 140. FIG. 5g shows lower wall 110 of the test channel with upper wall assembly 407 detached from the lower wall 110, where fiber optics cables 238 are in communication with the microprocessor for the operation of the reflective optical sensors. When upper wall assembly 407 is detached, reflective optical sensor 278 and electrode 140 of the renewable biosensor are accessible for thorough cleaning. FIG. 8a shows upper wall assembly 407 attached to brush head 406 while FIG. 8b shows upper wall assembly 407 detached for cleaning purposes. Upper wall assembly 407 is attached to brush head 406 by any suitable self-locating, snap-on fastening mechanism. A combination of the different sets of sensors provides a broad capability for detecting abnormalities for ensuring the consistency of measured data and for reliability of diagnostics. In the foregoing embodiment, means for including saliva monitoring and diagnostics capability in an electrical toothbrush have been described.

Figure 5H:
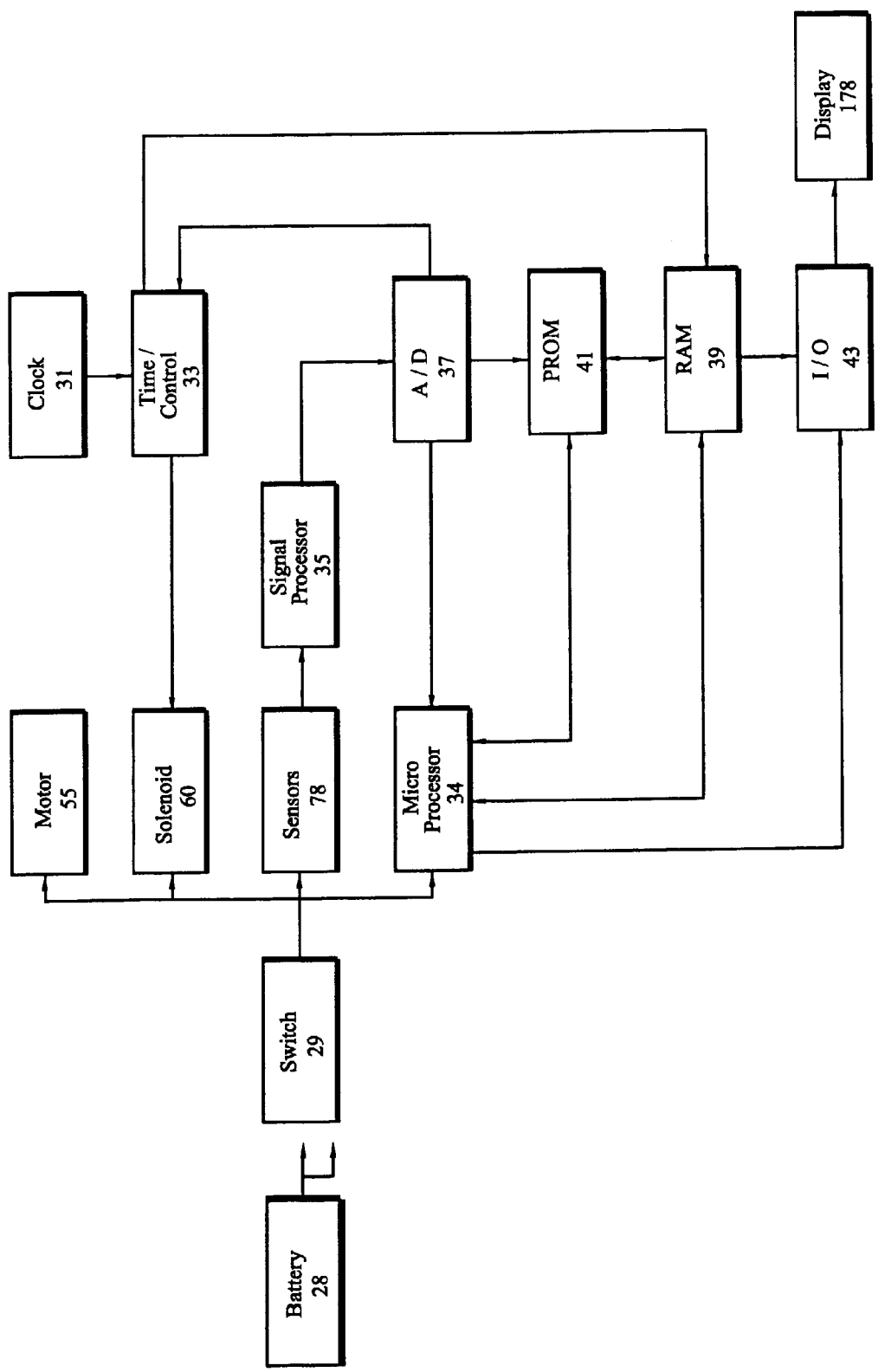
FIG. 5h is a block diagram of the components of the saliva-monitoring toothbrush.
Figure 51:
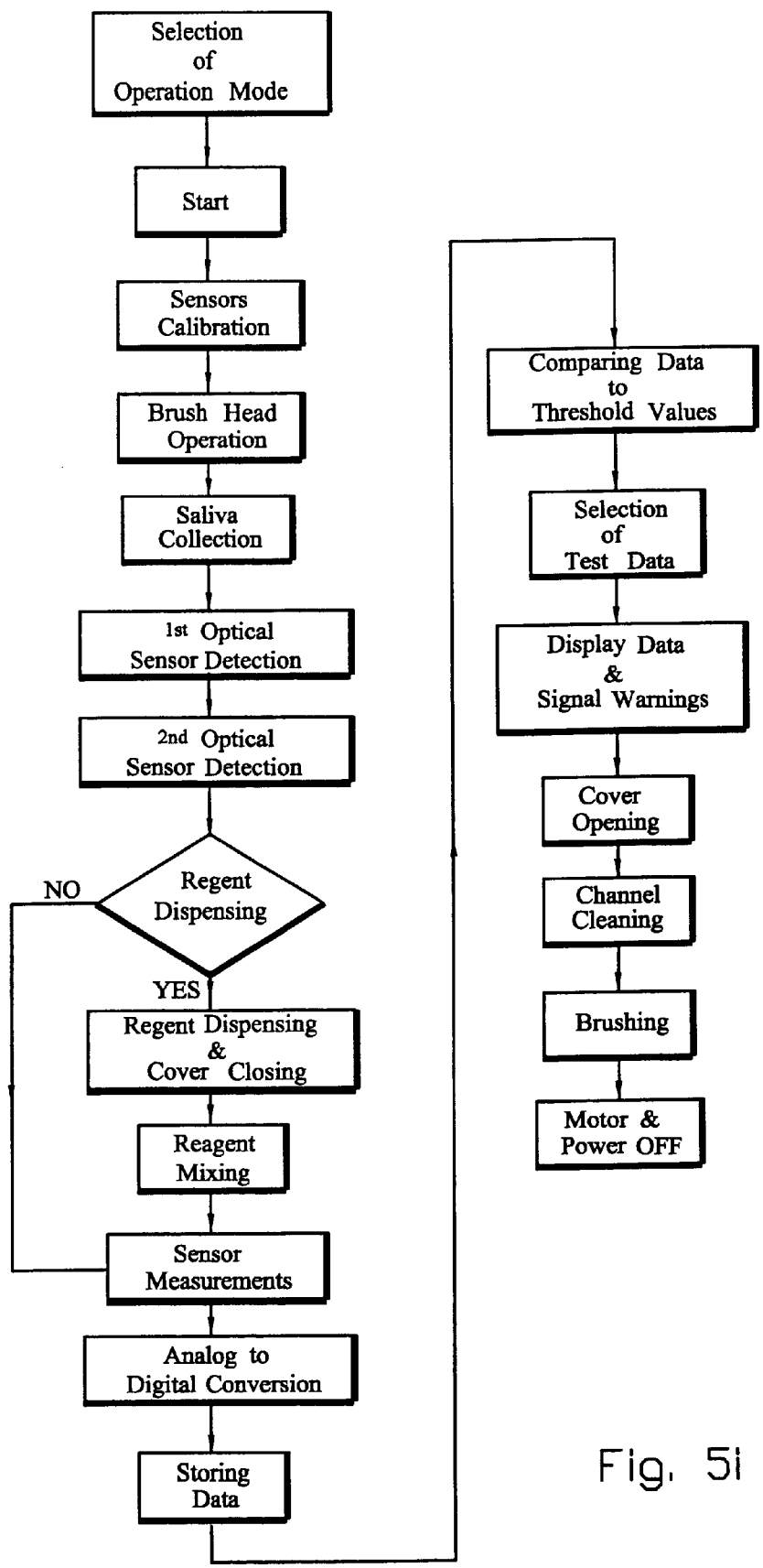

A block diagram of the electrical components of the toothbrush of this invention is shown in FIG. 5h. Battery 28 provides power to all the electrical components of the toothbrush. The switch unit 29 has multiple switches for independently activating motor 55, solenoid 60, sensors 78 and microprocessor 34. A clock 31 provides input to a timer/control unit 33, which controls the timing for activating the solenoid 60. Sensors 78 are connected to a signal processor 35, which amplifies signals received from the sensors and filters the amplified signals as input to the A/D converter 37, which converts the analog signals into digital signals for input to the microprocessor 34. The microprocessor has a random access memory (RAM) unit 39 and a programmable read only memory (PROM) unit 41. The RAM unit contains programming related to the operation of the electrical components and the PROM contains algorithm software for sensor signal calibration and calculation of the concentrations of targeted analytes based on the output of the A/D converter. The information stored in RAM unit 39 is read through I/O 43. Display unit 178 displays trend data of analytes in saliva samples and provides warning signals if established threshold values are exceeded.

A self-explanatory, corresponding flow chart of the operation of the electrical toothbrush as described herein shown in FIG. 5i.

Figures 6A, 6B:
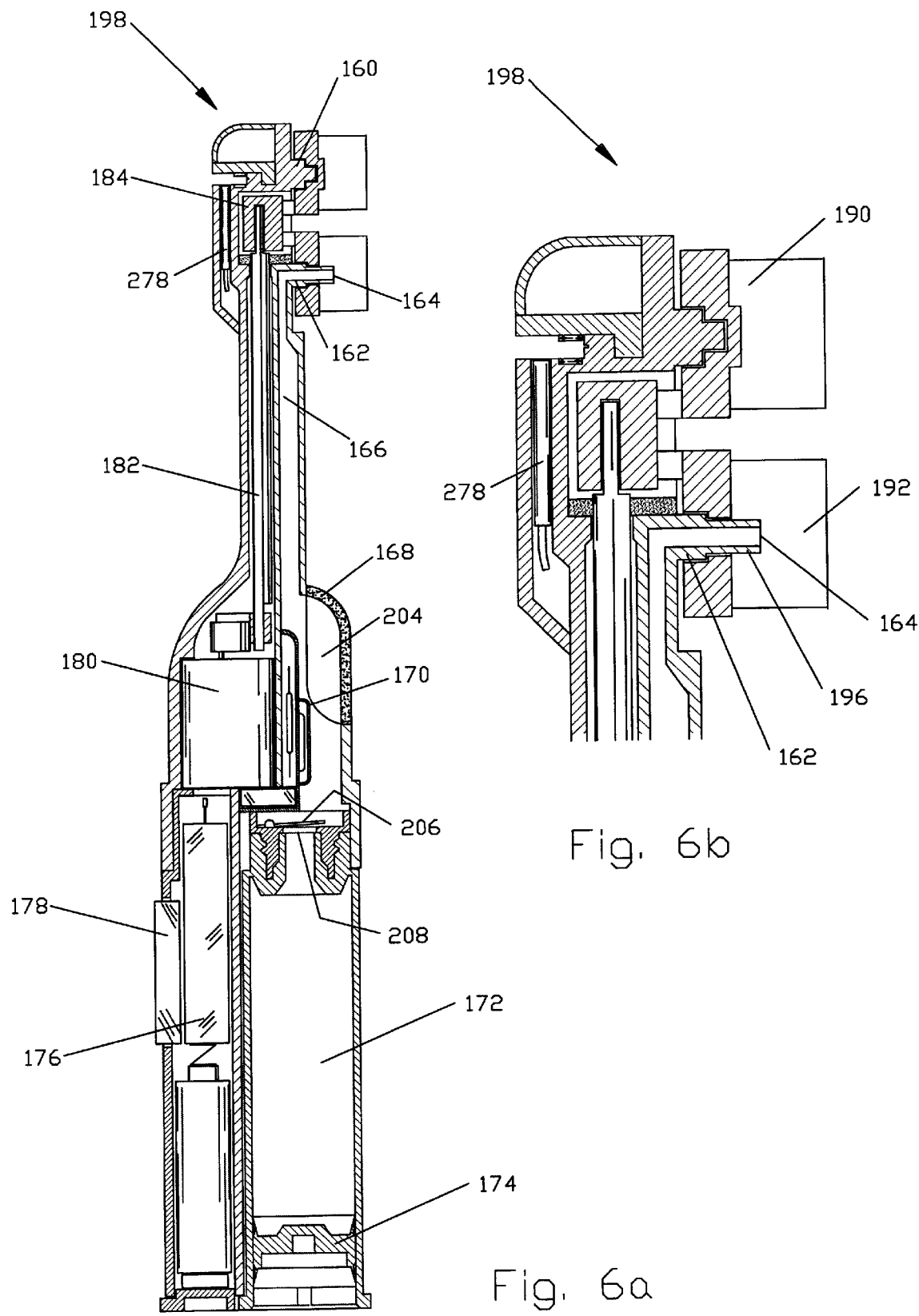

In another embodiment, the invention includes a saliva-monitoring toothbrush which has dentifrice-dispensing capability. FIG. 6a shows a saliva-monitoring electrical toothbrush having a dentifrice dispenser for convenience and portability. Referring to FIG. 6a and FIG. 6b, the brush head 198 includes a test channel, sensors, a first bristle element 190 and a second bristle element 192. Detailed descriptions of the oscillation mechanism for the bristle elements and the dispensing mechanism are set forth in copending U.S. patent application Ser. No. 09/649,074 filed Aug. 28, 2000. Therefore, only a brief description is provided here. The first bristle element 190 is mounted on the first post 160 of the brush head 198. The second bristle element 192, however, has a through hole on its platform and the hole is mounted on the outer surface of the wall 196 of the spout opening 164 of the second post 162 on the brush head. The spout opening 164 is connected to a flow channel 166 that is in communication with a pump chamber 204. Pump chamber 204 includes elastic button 168, a one-way check valve 206, and an inlet opening 208 that is connected to cartridge 172 containing dentifrice material. Cartridge 172 has a follower disk 174 for packing the dentifrice material when the dentifrice material is being pumped out. When elastic button 168 is depressed, the hydraulic pressure causes the one-way check valve 206 to close and the dentifrice material is forced to flow to the top of bristles through the flow channel 166 and the spout opening 164. At the same time, the hydraulic pressure activates internal switch 170 to cause the oscillation of the bristle elements. When the elastic button 168 is released, the follower disk 174 moves forward to push dentifrice material from the cartridge 172 to the pumping chamber to replace the volume dispensed. The operation of the dentifrice dispensing is completely independent of the electrical operations of the test channel measurements and the oscillation of the bristle elements.

In another embodiment of the invention, the test channel is positioned on the side surface of the brush head. It is formed by the gap between opposing electrodes which are spaced apart on the side surface in a manner such that the electrodes are the test channel walls. FIGS. 9a and 9b show test channel matrix 510 positioned on side surface 526 of brush head 506. FIG. 9c is an enlarged view of test channel matrix 510 having test channels 520 as shown in FIG. 9b. Test channel matrix 510 consists of an electrode matrix having electrode 516, counter electrode 514 and insulating layer 524 which wraps around the external surfaces of electrode 516 and counter electrode 514 but does not cover the surfaces which are channel walls 521. Electrodes 516 and counter electrode 514 are positioned on side surface 526 of brush head 506 and are spaced apart so that test channels 520 are formed by the gaps between them. Test channel walls 521 are the exposed surfaces of the electrodes and counter electrode. Leads 530 and 531 and connectors 538 and 539 carry sensing signals to a microprocessor contained in the brush handle. In operation, test channels 520 are filled with a quantity of saliva by capillary action by immersing test channel matrix 510 in a saliva pool. The surface tension of the saliva retains the quantity inside test channels 520 for measurements. Upon command from the microprocessor, the electrodes provide a sensing signal in the same manner as that previously described for the biosensor electrode matrix of FIG. 4a. External test channel matrix 510 provides conductivity measurements without the use of a reagent. This embodiment is particularly applicable for monitoring ovulation as referenced in the prior art.

Figure 10B:
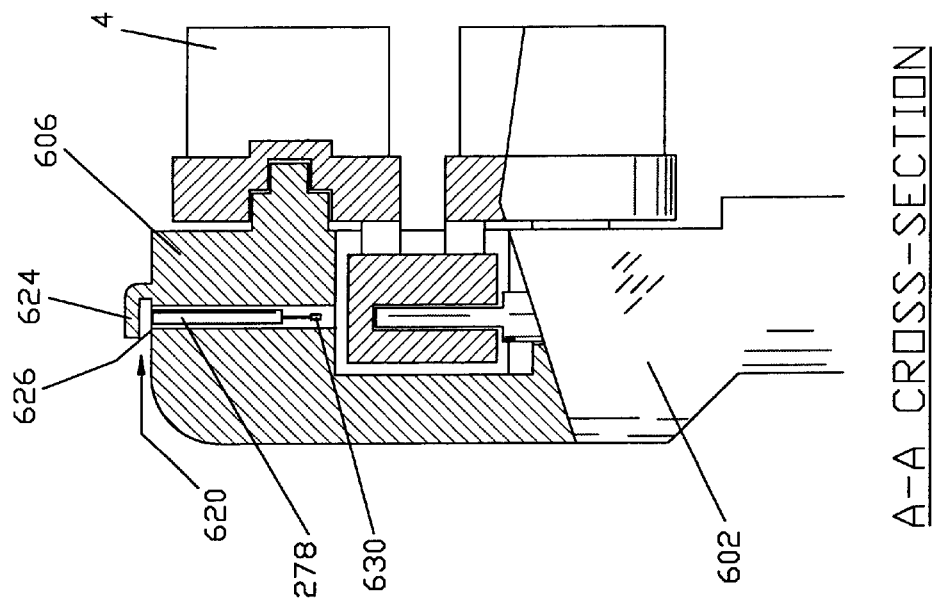
Figure 10A:
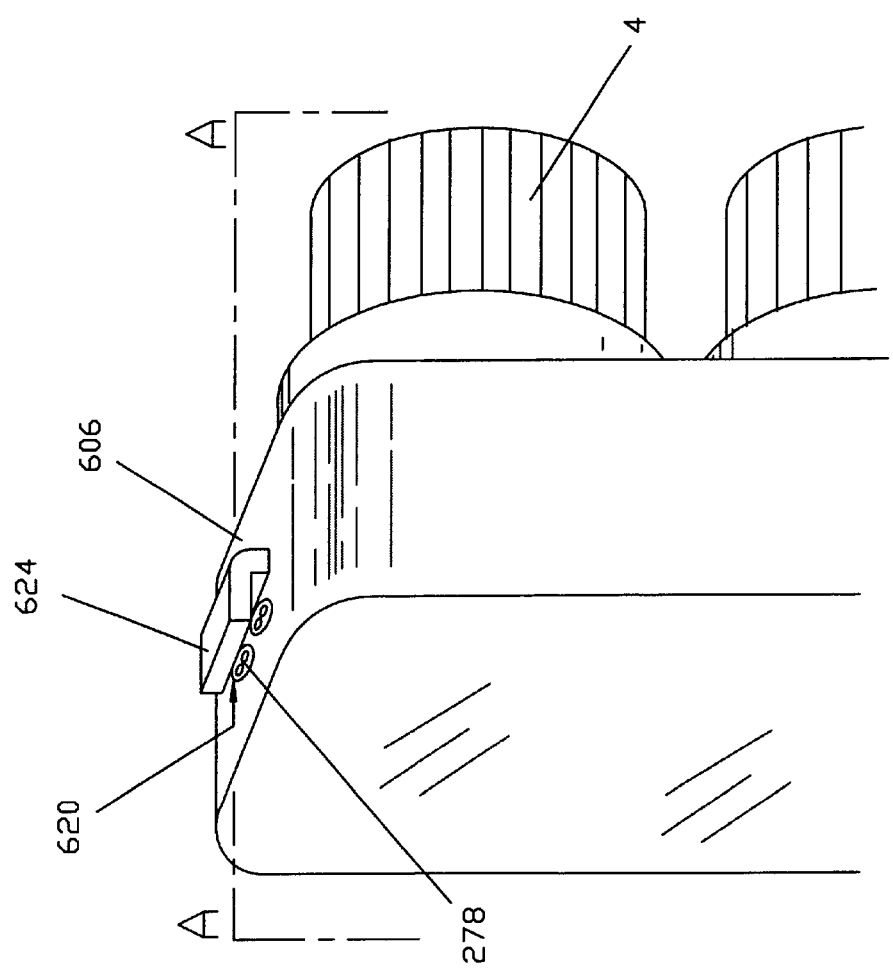
FIG. 10a is a perspective view of a brush head which has an open test channel having a reflective optical sensor positioned on a side surface of a brush head.

FIGS. 10a and 10b show another configuration of a test channel positioned on side surface 626 of brush head 606. Test channel 620 is formed by the gap between side surface 626 and upper wall 624 which extends from side surface 626. Test channel 620 is equipped with reflective optical sensor 278 which is positioned on side surface 626 and opposed to upper wall 624. The channel gap between upper wall 624 and side surface 626 is sufficiently narrow to induce capillary flow and to retain a saliva specimen in test channel 620 by surface tension forces, yet is sufficiently wide to allow for the passage of cleaning water to flush out saliva within the channel. Leads 630 transmit sensing signals from reflective optical sensors 278 to a microprocessor contained in the brush handle. In operation, a quantity of saliva is drawn into test channel 620 by capillary action by immersing the test channel into a pool of saliva. Surface tension forces retain saliva in the test channel for measurements. Upon command of the microprocessor, optical sensor 278 detects the reflectance signal of the saliva sample. The signal is transmitted to the microprocessor which produces readable and/or storable signals for the tested property. The types of test channels shown and described in FIGS. 9a and 10a may be placed on one brush head to enhance the monitoring of saliva samples.

Another embodiment of the invention utilizes a hydrophobic air filter to remove pockets of air from saliva in the test channel. Typical hydrophobic air filter methods and materials useful for this purpose are described in U.S. Pat. No. 5,988,426 to Stem and U.S. Pat. No. 6,176,903 to Wamsiedler. While vibration of the brush head stimulates saliva secretions and reduces air pockets within a saliva specimen, the use of a hydrophobic air filter facilitates removal of any residual air pockets. As shown in FIGS. 11a, 11b and 11c, a hydrophobic filter material 430, that is gas permeable and liquid impermeable, is placed in the upper wall of test channel 420 and on leading edge or ceiling 432 of the detachable channel wall assembly 417 of a brush head. The hydrophobic material can also be placed in other selected areas such as in lower wall 410. The pore size of the hydrophobic material 430 such as polytetrafluoroethylene is optimally determined to allow for the free passage of air 442 while blocking the passage of saliva and water through the channel wall. As the capillary saliva flow 440 enters test channel 420, entrapped air pockets tend to migrate to the front and boundary of the progressing flow. Once surfacing on the edges of the flow, the air bubbles burst into the pores of the hydrophobic material 430 and are released from the saliva flow. This venting and filtering function effectively de-gas the saliva. Furthermore, the patch of hydrophobic material 430 positioned on ceiling 432 of the detachable channel wall assembly 417 allows pressure equalization between air inside of compartment 433 of the detachable channel wall assembly 417 and the ambient atmospheric pressure. Airflow also occurs through hydrophobic material 430 when the test channel becomes empty after cleaning. When the brush head is not in use, the hydrophobic material helps ventilate the test channel during the drying process.

Figure 7:
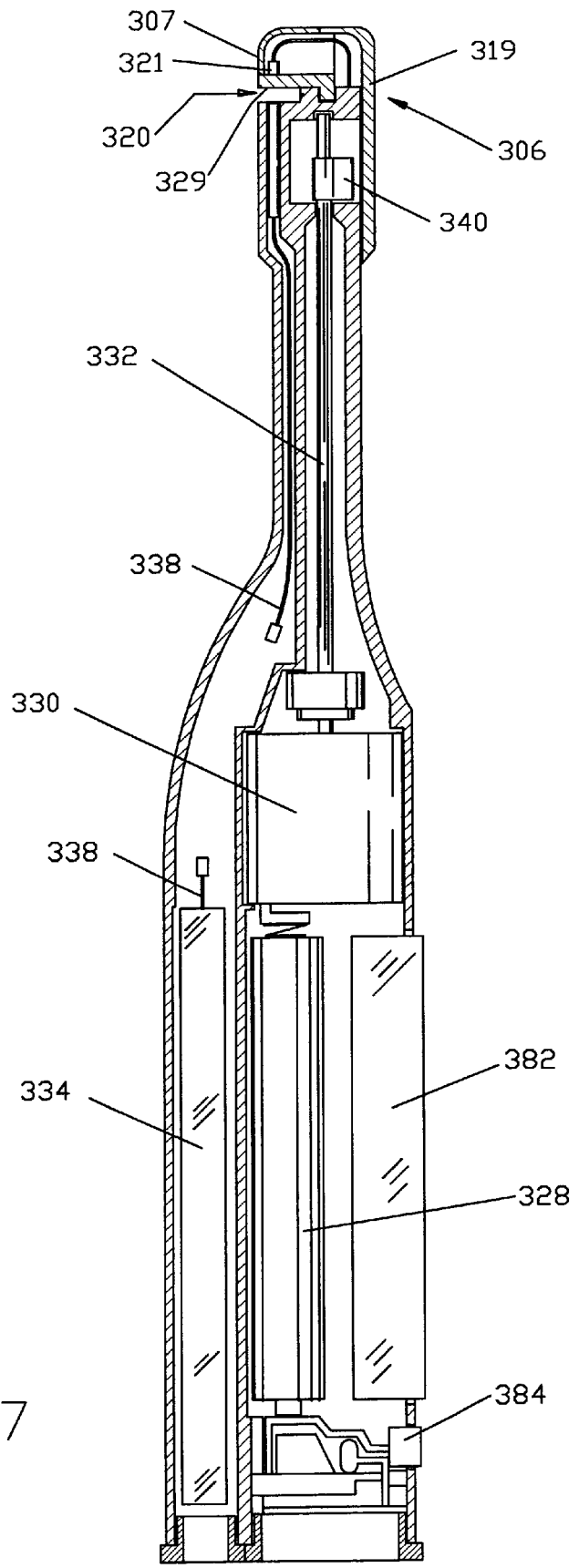
FIG. 7 is a section view of a saliva-monitoring oral device having an open test channel on a test head.

The methods of saliva stimulation, collection and the configuration of the test channel are applicable to any hand-held device with or without bristle elements. FIG. 7 shows a saliva-monitoring oral device which is substantially the same as the toothbrush shown and described in FIG. 1a except that the test channel is housed in test head 306 instead of in a brush head. While there are no bristles mounted on test head 306, the device functions in the same manner as the saliva monitoring electrical toothbrush except that it is not used for teeth cleaning purposes.

The present invention has been described in detail with reference to preferred embodiments thereof However, variations and modifications can be implemented within the spirit and scope of this invention. For example, as an oral device, the bristle elements can be replaced by a gum massaging element, a dental floss, a toothpick, a tongue scraper or other element used for dental or medical functions such as an oral thermometer. The open test channel can be in a form of any elongated cavity with or without a detachable wall for cleaning and the vent groove can be replaced by an aperture for releasing entrapped air. The one-way check valve can be a split membrane rather than a hinged film. Instead of an optical sensor, a pH sensor, a colormetric sensor or an elaborated integrated sensor system can be used in the test channel for measurements. Furthermore, the channel cover and the reagent dispensing can be operated manually rather than automatically by electromechanical means.

I claim:

1. A saliva-monitoring electrical toothbrush comprising:
   a. a handle;
   b. a brush head attached to the handle, said brush head having a top surface, a bottom surface, a side surface that extends from the top surface to the bottom surface and a test channel which is capable of retaining a test sample of saliva by capillary force;
   c. a plurality of bristles attached to the top surface of the brush head;
   d. sensing means in communication with the test channel for providing an output sensing signal representative of the tested properties of saliva collected in said test channel;

e. signal processing means for converting the output sensing signal to readable or storable information, said signal processing means having an input means for receiving the output sensing signal and an output means for producing a signal for information display or storage; and f. a power source attached to said handle for energizing the sensing means and the signal processing means.

2. The saliva-monitoring electrical toothbrush of claim 1 including a driving means for imparting an oscillating or rotating motion to the bristles and for imparting a vibrating motion to the brush head.

3. The saliva-monitoring electrical toothbrush of claim 1 wherein the plurality of bristles are attached to a brush element which is detachably mounted to the top surface of the brush head.

4. The saliva-monitoring electrical toothbrush of claim 1 including a reservoir for storing dentifrice material in said handle and means for pumping the dentifrice material from the reservoir to the bristles attached to the brush head.

5. The saliva-monitoring electrical toothbrush of claim 1 wherein the signal processing means is a microprocessor.

6. The saliva-monitoring electrical toothbrush of claim 1 wherein the sensing means is comprised of one or more sensors.

7. The saliva-monitoring electrical toothbrush of claim 1 including a reservoir for storing a reagent, and dispensing means for delivering a controlled quantity of a reagent from the reservoir into the test channel.

8. The saliva-monitoring electrical toothbrush of claim 7 wherein the dispensing means includes a resilient elastic button for applying pressure to force the flow of reagent from the reservoir to the test channel.

9. The saliva-monitoring electrical toothbrush of claim 7 wherein the reservoir includes a replaceable cartridge containing a reagent.

10. The saliva-monitoring electrical toothbrush of claim 1 wherein the test channel is positioned in a recess in the bottom surface of the brush head.

11. The saliva-monitoring electrical toothbrush of claim 10 wherein the test channel is comprised of a base and opposing upper and lower walls which extend from the base and are spaced apart from each other to form a test channel opening.

12. The saliva-monitoring electrical toothbrush of claim 11 wherein the sensing means includes at least one electrode matrix having a plurality of electrodes and counter electrodes, said electrode matrix being positioned on at least one wall of the test channel.

13. The saliva-monitoring electrical toothbrush of claim 11 wherein:

a. the sensing means is comprised of a renewable biosensor system which includes at least one reusable electrode matrix having a plurality of electrodes and counter electrodes, said electrode matrix being positioned on at least one wall of the test channel; and b. the test channel has an opening in the same wall where the electrode matrix is positioned for the inflow of a controlled quantity of reagent into the test channel to form a mixture with saliva, said mixture being removable from the electrode matrix and from the test channel by a cleansing liquid.

14. The saliva-monitoring electrical toothbrush of claim 11 wherein the sensing means is comprised of a fiber optic sensor positioned in the test channel walls.

15. The saliva-monitoring electrical toothbrush of claim 11 including a filter to vent air from the test channel, said filter being gas permeable and liquid impermeable and being positioned in the upper wall of the test channel.

16. The saliva-monitoring electrical toothbrush of claim 11 in which the upper wall of the test channel is detachable from the channel.

17. The saliva-monitoring electrical toothbrush of claim 11 including a channel cover for the test channel opening.

18. The saliva-monitoring electrical toothbrush of claim 17 wherein the channel cover is slidable to an open and a closed position and comprises:

a. a saddle-shaped base with an opening therethrough which coincides with the channel opening when the channel cover is in an open position; and b. guide ribs on the underside of the saddle-shaped base for engaging with slots in the side surface of the brush head and for guiding the sliding movement of the channel cover to its open and closed positions when said guide ribs are engaged in said slots.

19. The saliva-monitoring electrical toothbrush of claim 18 wherein the movement of the channel cover to its open and closed positions is driven by a motor contained in the handle.

20. The saliva-monitoring electrical toothbrush of claim 18 wherein the channel cover is moved automatically to its closed position in response to the dispensing action of a reagent from a reservoir into the test channel.

21. The saliva-monitoring electrical toothbrush of claim 1 wherein the test channel is positioned on the side surface of the brush head.

22. The saliva-monitoring electrical toothbrush of claim 21 wherein at least one electrode and opposing counter electrode are positioned on the side surface of the brush head and are spaced apart from each other to create a gap comprising the test channel, said electrode and counter electrode providing an output sensing signal representative of the tested properties of the retained saliva.

23. The saliva-monitoring electrical toothbrush of claim 21 wherein the test channel has an upper wall which extends from the side surface of the brush head and a reflective optical sensor which is positioned on the side surface opposed to said upper wall.

24. The saliva-monitoring electrical toothbrush of claim 23 including a filter to vent air from the test channel, said filter being gas permeable and liquid impermeable and being positioned in the upper wall of the test channel.

* * * * *